(12) United States Patent
Wang et al.

(10) Patent No.: US 11,028,398 B2
(45) Date of Patent: *Jun. 8, 2021

(54) FUSION PROTEINS HAVING MUTATED IMMUNOGLOBULIN HINGE REGION

(75) Inventors: Haitao Wang, Vancouver (CA); Yong Du, Vancouver (CA); Rui Zhang, Vancouver (CA); Jing Xu, Vancouver (CA); Longbin Liu, Beijing (CN)

(73) Assignee: NOVAGEN HOLDING CORPORATION, George Town (KY)

( * ) Notice: Subject to any disclaimer, the term of this patent is extended or adjusted under 35 U.S.C. 154(b) by 0 days.

This patent is subject to a terminal disclaimer.

(21) Appl. No.: 13/275,205

(22) Filed: Oct. 17, 2011

(65) Prior Publication Data

US 2012/0100099 A1  Apr. 26, 2012

Related U.S. Application Data

(63) Continuation of application No. 12/180,455, filed on Jul. 25, 2008, now Pat. No. 8,067,548.

(60) Provisional application No. 60/952,181, filed on Jul. 26, 2007.

(51) Int. Cl.
| | |
|---|---|
| *C07K 1/00* | (2006.01) |
| *A61K 45/00* | (2006.01) |
| *A61K 39/00* | (2006.01) |
| *C12N 15/62* | (2006.01) |
| *A61K 47/68* | (2017.01) |
| *C07K 16/00* | (2006.01) |

(52) U.S. Cl.
CPC .......... *C12N 15/62* (2013.01); *A61K 47/6811* (2017.08); *A61K 47/6835* (2017.08); *C07K 2317/53* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,116,964 A | 5/1992 | Capon | |
| 5,618,698 A | 4/1997 | Lin | |
| 5,908,626 A | 6/1999 | Chang et al. | |
| 5,916,773 A | 6/1999 | Mele et al. | |
| 6,096,871 A | 8/2000 | Presta et al. | |
| 6,165,476 A | 12/2000 | Strom et al. | |
| 6,403,077 B1 | 6/2002 | Strom et al. | |
| 6,548,653 B1 | 4/2003 | Young et al. | |
| 6,586,398 B1 | 7/2003 | Kinstler et al. | |
| 6,660,843 B1 | 12/2003 | Feige et al. | |
| 6,750,334 B1 | 6/2004 | Gray et al. | |
| 6,797,493 B2 | 9/2004 | Sun et al. | |
| 6,808,902 B1 | 10/2004 | Treuheit et al. | |
| 6,821,505 B2 | 11/2004 | Ward | |
| 6,900,292 B2 | 5/2005 | Sun et al. | |
| 6,936,439 B2 | 8/2005 | Mann et al. | |
| 6,987,006 B2 | 1/2006 | Fleer et al. | |
| 6,989,365 B2 | 1/2006 | Fleer et al. | |
| 7,030,226 B2 | 4/2006 | Sun et al. | |
| 7,041,478 B2 | 5/2006 | Fleer et al. | |
| 7,056,701 B2 | 6/2006 | Fleer et al. | |
| 7,250,493 B2 | 7/2007 | Sun et al. | |
| 7,253,264 B1 | 8/2007 | Lauffer et al. | |
| 7,625,564 B2 | 12/2009 | Wang et al. | |
| 7,964,375 B2 | 6/2011 | Wang et al. | |
| 8,067,548 B2 | 11/2011 | Wang et al. | |
| 8,431,132 B2 | 4/2013 | Wang et al. | |
| 9,375,487 B2 | 6/2016 | Wang et al. | |
| 2003/0044423 A1 | 3/2003 | Gilles et al. | |
| 2003/0235536 A1* | 12/2003 | Blumberg et al. | 424/45 |
| 2004/0063912 A1 | 4/2004 | Blumberg et al. | |
| 2004/0127682 A1* | 7/2004 | Neville et al. | 530/350 |
| 2004/0175824 A1 | 9/2004 | Sun et al. | |
| 2005/0048572 A1 | 3/2005 | Reilly et al. | |
| 2005/0124045 A1 | 6/2005 | Sun et al. | |
| 2005/0202538 A1 | 9/2005 | Gillies et al. | |
| 2005/0238646 A1 | 10/2005 | Ledbetter et al. | |
| 2005/0260194 A1 | 11/2005 | Peters et al. | |
| 2006/0025573 A1 | 2/2006 | Gillies et al. | |
| 2006/0134105 A1 | 6/2006 | Lazar et al. | |
| 2007/0065440 A1 | 3/2007 | Tomlinson et al. | |

(Continued)

FOREIGN PATENT DOCUMENTS

| | | |
|---|---|---|
| CA | 2045869 A1 | 12/1991 |
| CA | 2328490 A1 | 11/1999 |

(Continued)

OTHER PUBLICATIONS

Roopenian et al. Nature Review Immunology 2007, 7:715-725.*
Martin et al. Molecular Cell. 2001, vol. 7, 867-877.*
Brekke et al. The Immunologist. 1994 2:125-130.*
Ashkenazi et al. Current Opinion in Immunology 1997, 9:195-200.*
Amoresano, A., et al,. "Structural characterization and independent folding of a chimeric glycoprotein comprising granulocyte-macrophage colony stimulating factor and erythropoietin sequences", Glycobiology, Aug. 1998, 8(6): 779-790.
Bitonti, A.J., et al., "Pulmonary delivery of an erythropoietin Fc fusion protein in non-human primates through an immunoglobulin transport pathway", Proc Natl Acad Sci USA, Jun. 2004, 101(26):9763-9768.

(Continued)

*Primary Examiner* — Chun W Dahle
(74) *Attorney, Agent, or Firm* — Seed Intellectual Property Law Group LLP

(57) ABSTRACT

A fusion protein having a non-immunoglobulin polypeptide having a cysteine residue proximal to the C terminal thereof, and an immunoglobulin component with a mutated hinge region is provided. The mutation comprises a point mutated site corresponding in position to the position in a native hinge region of the cysteine residue located nearest the cysteine residue of the non-Ig component. The distance from the cysteine residue of the non-immunoglobulin polypeptide and any remaining cysteine residues of the mutated hinge region is sufficient to prevent the formation of a disulphide bond therebetween.

25 Claims, 18 Drawing Sheets

Specification includes a Sequence Listing.

(56) References Cited

U.S. PATENT DOCUMENTS

| | | | |
|---|---|---|---|
| 2007/0178112 | A1 | 8/2007 | Wang et al. |
| 2007/0269371 | A1 | 11/2007 | Krummen et al. |
| 2008/0260746 | A1 | 10/2008 | Abderrahim et al. |
| 2009/0081218 | A1 | 3/2009 | Wang et al. |
| 2009/0297522 | A1 | 12/2009 | Wang et al. |
| 2010/0098716 | A1 | 4/2010 | Wang et al. |
| 2010/0099145 | A1 | 4/2010 | Wang et al. |
| 2012/0100099 | A1 | 4/2012 | Wang et al. |
| 2017/0114110 | A1 | 4/2017 | Wang et al. |

FOREIGN PATENT DOCUMENTS

| | | | |
|---|---|---|---|
| EP | 464533 | A1 | 1/1992 |
| WO | 99/02709 | A1 | 1/1999 |
| WO | 99/58662 | A1 | 11/1999 |
| WO | 99/66054 | A2 | 12/1999 |
| WO | 01/03737 | A1 | 1/2001 |
| WO | 01/30320 | A1 | 5/2001 |
| WO | 01/36489 | A2 | 5/2001 |
| WO | 01/76640 | A2 | 10/2001 |
| WO | 01/81405 | A2 | 11/2001 |
| WO | 02/48194 | A1 | 6/2002 |
| WO | 02/056910 | A1 | 7/2002 |
| WO | 02/072605 | A2 | 9/2002 |
| WO | 03/046013 | A1 | 6/2003 |
| WO | 03/048210 | A1 | 6/2003 |
| WO | 2004/004798 | A2 | 1/2004 |
| WO | 2004/101739 | A2 | 11/2004 |
| WO | 2005/001025 | A2 | 1/2005 |
| WO | 2005/063808 | A1 | 7/2005 |
| WO | 2005/079232 | A2 | 9/2005 |
| WO | 2005/100395 | A2 | 10/2005 |
| WO | 2006/079169 | A1 | 8/2006 |
| WO | 2007/085084 | A1 | 8/2007 |

OTHER PUBLICATIONS

Burgess, Wilson H., et al., "Possible dissociation of the heparin-binding and mitogenic activities of heparin-binding (acidic fibroblast) growth factor-1 from its receptor-binding activity by site-directed mutagenesis of a single lysine residue", Journal of Cell Biology, 1990, 111:2129-2138.

Chica, R.A., et al. "Semi-rational approaches to engineering enzyme activity: combining the benefits of directed evolution and rational design", Curr Opin Biotechnol, 2005, 16(4):378-384.

Coscarella, A., et al., "Pharmacokinetic and immunogenic behavior of three recombinant human GM-CSF-EPO hybrid proteins in cynomolgus monkeys", Mol Biotechnol, Oct. 1998, 10(2):115-122.

Coscarella, A., et al., "Production of recombinant human GM-CSF-EPO hybrid proteins: in vitro biological characterization", Eur J Haematol, Oct. 1997, 59(4):238-246.

Dalle B, et al., "Dimeric erythropoietin fusion protein with enhanced erythropoietic activity in vitro and in vivo", Blood, Jun. 15, 2001; 97(12):3776-3782.

Dumont, J.A., et al., "Delivery of an erythropoietin-Fc fusion protein by inhalation in humans through an immunoglobulin transport pathway", J Aerosol Med.; 2005 Fall;18(3):294-303.

Lazar, Eliane, et al., "Transforming growth factor alpha: mutation of aspartic acid 47 and leucine 48 results in different biological activities", Molecular and Cellular Biology, 1988, 8(3):1247-1252.

Lee, D.E., et al., "The prolonged half-lives of new erythropoietin derivatives via peptide addition", Biochem Biophys Res Commun, Jan. 6, 2006, 339(1):380-385; Epub Nov. 14, 2005.

Schriebl, K., et al., "Biochemical characterization of rhEpo-Fc fusion protein expressed in CHO cells", Protein Expression & Purification, Oct. 2006, 49(2):265-275.

Sen, S., et al., "Developments in directed evolution for improving enzyme functions", Appl Biochem Biotechnol, 2007, 143(3):212-223.

Skolnick, Jeffrey and Jacquelyn S. Fetrow, "From genes to protein structure and function: novel applications of computation approaches in the genomic era", Trends in Biotechnology, 2000, 18:34-39.

Su, L, et al., "High-level expression of human stem cell factor fused with erythropoietin mimetic peptide in *Escherichia coli*", Protein Expr Purif; Jun. 2006, 47(2):477-482; Epub Nov. 28, 2005.

Sytkowski, A.J., et al., "An erythropoietin fusion protein comprised of identical repeating domains exhibits enhanced biological properties", J Biol Chem, Aug. 27, 1999, 274(35):24773-8.

Way, J.C. et al., "Improvement of Fc-erythropoietin structure and pharmacokinetics by modification at a disulfide bond", Protein Engineering, Design & Selection, Mar. 2005, 18(3):111-118.

[U.S. Appl. No. 11/340,661] Office Action (Restriction Requirement) dated Mar. 17, 2008 for U.S. Appl. No. 11/340,661, Wang et al., filed Jan. 27, 2006 (now U.S. Pat. No. 7,625,564).

[U.S. Appl. No. 11/340,661] Office Action dated Jul. 10, 2008 for U.S. Appl. No. 11/340,661, Wang et al., filed Jan. 27, 2006 (now U.S. Pat. No. 7,625,564).

[U.S. Appl. No. 11/340,661] Office Action dated Mar. 5, 2009 for U.S. Appl. No. 11/340,661, Wang et al., filed Jan. 27, 2006 (now U.S. Pat. No. 7,625,564).

[U.S. Appl. No. 11/340,661] Office Action dated Jul. 22, 2009 for U.S. Appl. No. 11/340,661, Wang et al., filed Jan. 27, 2006 (now U.S. Pat. No. 7,625,564).

[U.S. Appl. No. 11/340,661]—Notice of Allowance dated Aug. 13, 2009 for U.S. Appl. No. 11/340,661, Wang et al., filed Jan. 27, 2006 (now U.S. Pat. No. 7,625,564).

[U.S. Appl. No. 12/162,320]—Office Action (Restriction Requirement) dated Apr. 2, 2010 for U.S. Appl. No. 12/162,320, Wang, et al., filed Jan. 27, 2007, which is a 371 of International Application No. PCT/CA2007/000107, which is a CIP of U.S. Appl. No. 11/340,661, Wang et al., filed Jan. 27, 2006 (now U.S. Pat. No. 7,625,564).

[U.S. Appl. No. 12/162,320]—Office Action dated Aug. 19, 2010 for U.S. Appl. No. 12/162,320, Wang, et al., filed Jan. 27, 2007, which is a 371 of International Application No. PCT/CA2007/000107, which is a CIP of U.S. Appl. No. 11/340,661, Wang et al., filed Jan. 27, 2006 (now U.S. Pat. No. 7,625,564).

[U.S. Appl. No. 12/162,320]—Terminal Disclaimer filed Feb. 21, 2011 for U.S. Appl. No. 12/162,320, Wang et al., filed Jan. 27, 2007, which is a 371 of International Application No. PCT/CA2007/000107, which is a CIP of U.S. Appl. No. 11/340,661, Wang et al., filed Jan. 27, 2006 (now U.S. Pat. No. 7,625,564).

[U.S. Appl. No. 12/162,320]—Office Action dated May 4, 2011 for U.S. Appl. No. 12/162,320, Wang et al., filed Jan. 27, 2007, which is a 371 of International Application No. PCT/CA2007/000107, which is a CIP of U.S. Appl. No. 11/340,661, Wang et al., filed Jan. 27, 2006 (now U.S. Pat. No. 7,625,564).

[U.S. Appl. No. 12/180,455]—Office Action (Restriction Requirement) dated Jun. 16, 2009 U.S. Appl. No. 12/180,455, Wang et al., filed Jul. 25, 2008 (now U.S. Pat. No. 8,067,548).

[U.S. Appl. No. 12/180,455]—Office Action dated Oct. 15, 2009 U.S. Appl. No. 12/180,455, Wang et al., filed Jul. 25, 2008 (now U.S. Pat. No. 8,067,548).

[U.S. Appl. No. 12/180,455]—Office Action dated Aug. 3, 2010 U.S. Appl. No. 12/180,455, Wang et al., filed Jul. 25, 2008 (now U.S. Pat. No. 8,067,548).

[U.S. Appl. No. 12/180,455]—Office Action dated Feb. 25, 2011 for U.S. Appl. No. 12/180,455, Wang et al., filed Jul. 25, 2008 (now U.S. Pat. No. 8,067,548).

[U.S. Appl. No. 12/180,455]—Notice of Allowance dated Jul. 25, 2011, for U.S. Appl. No. 12/180,455, Wang et al., filed Jul. 25, 2008 (now U.S. Pat. No. 8,067,548).

[U.S. Appl. No. 12/555,742]—Office Action dated May 14, 2010 for U.S. Appl. No. 12/555,742, Wang et al., filed Sep. 8, 2009 (now U.S. Pat. No. 7,964,375), which is a divisional of U.S. Appl. No. 11/340,661, Wang et al., filed Jan. 27, 2006 (now U.S. Pat. No. 7,625,564).

[U.S. Appl. No. 12/555,742]—Notice of Allowance and Fees Due dated Feb. 14, 2011 for U.S. Appl. No. 12/555,742, Wang et al., filed Sep. 8, 2009 (now U.S. Pat. No. 7,964,375), which is a divisional of U.S. Appl. No. 11/340,661, Wang et al., filed Jan. 27, 2006 (now U.S. Pat. No. 7,625,564) (pp. 1-6).

(56) References Cited

OTHER PUBLICATIONS

[U.S. Appl. No. 12/555,743]—Office Action (Restriction Requirement) dated Mar. 7, 2011 for U.S. Appl. No. 12/755,743, Wang et al., filed Sep. 8, 2009, which is a divisional of U.S. Appl. No. 11/340,661, Wang et al., filed Jan. 27, 2006 (now U.S. Pat. No. 7,625,564).
[U.S. Appl. No. 12/555,743]—Notice of Allowance and Fees Due dated Oct. 11, 2011 for U.S. Appl. No. 12/555,743, Wang et al., filed Sep. 8, 2009, which is a divisional of U.S. Appl. No. 11/340,661, Wang et al., filed Jan. 27, 2006 (now U.S. Pat. No. 7,625,564).
Brekke et al., "The structural requirements for complement activation by IgG: does it hinge on the hinge?" *Immunology Today* 16(2):85-89, 1995.
Accession AR670085. Jun. 13, 2005.
Accession AR670085. Jun. 13, 2005. Protein to Nucleic Acid Alignment.
Singh et al., "Protein Engineering Approaches in the Post-Genomic Era," *Current Protein and Peptide Science* 18:1-11, 2017.

\* cited by examiner

2A

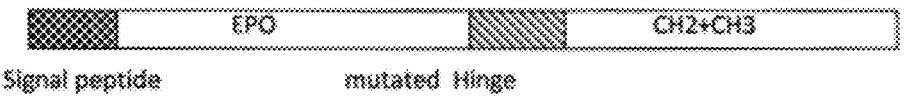

Signal peptide        mutated Hinge

2B

```
ATGGGGGTGCACGAATGTCCTGCCTGGCTGTGGCTTCTCCTGTCCCTGCTGTCGCTCCCT   60
 M  G  V  H  E  C  P  A  W  L  W  L  L  L  S  L  L  S  L  P
CTGGGCCTCCCAGTCCTGGGCGCCCCACCACGCCTCATCTGTGACAGCCGAGTCCTGGAG  120
 L  G  L  P  V  L  G  A  P  P  R  L  I  C  D  S  R  V  L  E
AGGTACCTCTTGGAGGCCAAGGAGGCCGAGAATATCACGACGGGCTGTGCTGAACACTGC  180
 R  Y  L  L  E  A  K  E  A  E  N  I  T  T  G  C  A  E  H  C
AGCTTGAATGAGAATATCACTGTCCCAGACACCAAAGTTAATTTCTATGCCTGGAAGAGG  240
 S  L  N  E  N  I  T  V  P  D  T  K  V  N  F  Y  A  W  K  R
ATGGAGGTCGGGCAGCAGGCCGTAGAAGTCTGGCAGGGCCTGGCCCTGCTGTCGGAAGCT  300
 M  E  V  G  Q  Q  A  V  E  V  W  Q  G  L  A  L  L  S  E  A
GTCCTGCGGGGCCAGGCCCTGTTGGTCAACTCTTCCCAGCCGTGGGAGCCCCTGCAGCTG  360
 V  L  R  G  Q  A  L  L  V  N  S  S  Q  P  W  E  P  L  Q  L
CATGTGGATAAAGCCGTCAGTGGCCTTCGCAGCCTCACCACTCTGCTTCGGGCTCTGCGA  420
 H  V  D  K  A  V  S  G  L  R  S  L  T  T  L  L  R  A  L  R
GCCCAGAAGGAAGCCATCTCCCCTCCAGATGCGGCCTCAGCTGCTCCACTCCGAACAATC  480
 A  Q  K  E  A  I  S  P  P  D  A  A  S  A  A  P  L  R  T  I
ACTGCTGACACTTTCCGCAAACTCTTCCGAGTCTACTCCAATTTCCTCCGGGGAAAGCTG  540
 T  A  D  T  F  R  K  L  F  R  V  Y  S  N  F  L  R  G  K  L
AAGCTGTACACAGGGGAGGCCTGCAGGACAGGGGACAGAGTTGAGCCCAAATCTGGTGAC  600
 K  L  Y  T  G  E  A  C  R  T  G  D  R  V  E  P  K  S  G  D
AAAACTAGTACATGCCCACCGTGCCCAGCACCTGAACTCCTGGGGGGACCGTCAGTCTTC  660
 K  T  S  T  C  P  P  C  P  A  P  E  L  L  G  G  P  S  V  F
CTCTTCCCCCCAAAACCCAAGGACACCCTCATGATCTCCCGGACCCCTGAGGTCACATGC  720
 L  F  P  P  K  P  K  D  T  L  M  I  S  R  T  P  E  V  T  C
GTGGTGGTGGACGTGAGCCACGAAGACCCTGAGGTCAAGTTCAACTGGTACGTGGACGGC  780
 V  V  V  D  V  S  H  E  D  P  E  V  K  F  N  W  Y  V  D  G
GTGGAGGTGCATAATGCCAAGACAAAGCCGCGGGAGGAGCAGTACAACAGCACGTACCGT  840
 V  E  V  H  N  A  K  T  K  P  R  E  E  Q  Y  N  S  T  Y  R
GTGGTCAGCGTCCTCACCGTCCTGCACCAGGACTGGCTGAATGGCAAGGAGTACAAGTGC  900
 V  V  S  V  L  T  V  L  H  Q  D  W  L  N  G  K  E  Y  K  C
AAGGTCTCCAACAAAGCCCTCCCAGCCCCCATCGAGAAAACCATCTCCAAAGCCAAAGGG  960
 K  V  S  N  K  A  L  P  A  P  I  E  K  T  I  S  K  A  K  G
CAGCCCCGAGAACCACAGGTGTACACCCTGCCCCCATCCCGGGATGAGCTGACCAAGAAC 1020
 Q  P  R  E  P  Q  V  Y  T  L  P  P  S  R  D  E  L  T  K  N
CAGGTCAGCCTGACCTGCCTGGTCAAAGGCTTCTATCCCAGCGACATCGCCGTGGAGTGG 1080
 Q  V  S  L  T  C  L  V  K  G  F  Y  P  S  D  I  A  V  E  W
GAGAGCAATGGGCAGCCGGAGAACAACTACAAGACCACGCCTCCCGTGCTGGACTCCGAC 1140
 E  S  N  G  Q  P  E  N  N  Y  K  T  T  P  P  V  L  D  S  D
GGCTCCTTCTTCCTCTACAGCAAGCTCACCGTGGACAAGAGCAGGTGGCAGCAGGGGAAC 1200
 G  P  F  F  L  Y  S  K  L  T  V  D  K  S  R  W  Q  Q  G  N
GTCTTCTCATGCTCCGTGATGCATGAGGCTCTGCACAACCACTACACGCAGAAGAGCCTC 1260
 V  F  S  C  S  V  M  H  E  A  L  H  N  H  Y  T  Q  K  S  L
TCCCTGTCTCCGGGTAAATAA                                        1320
 S  L  S  P  G  K  *
```

Figure 2

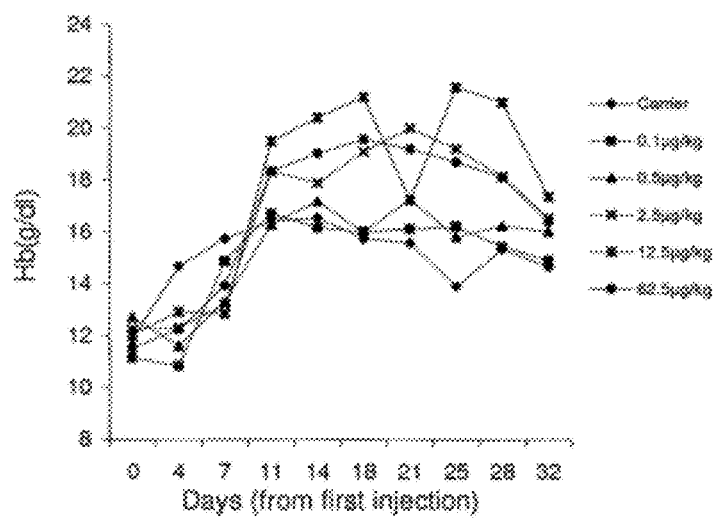
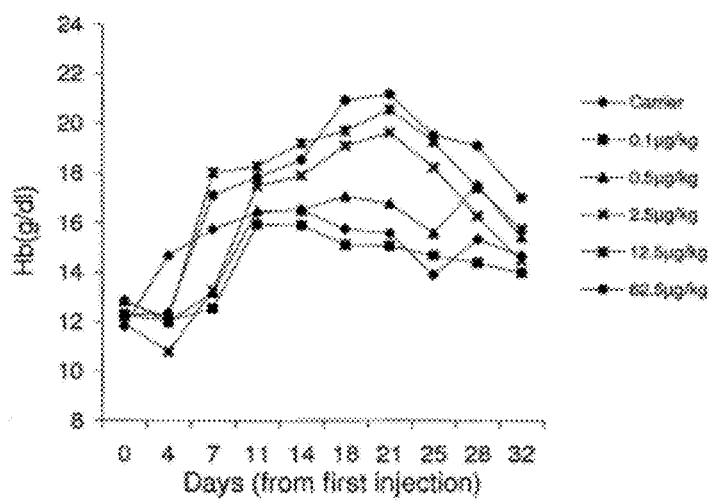
Figure 6

7A
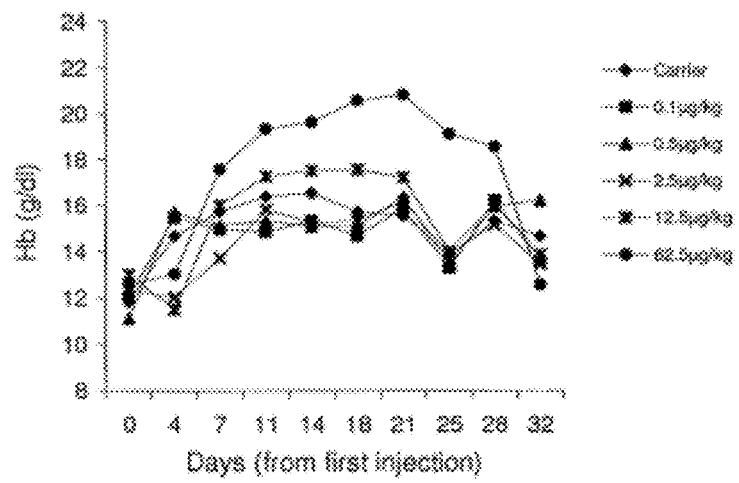
7B
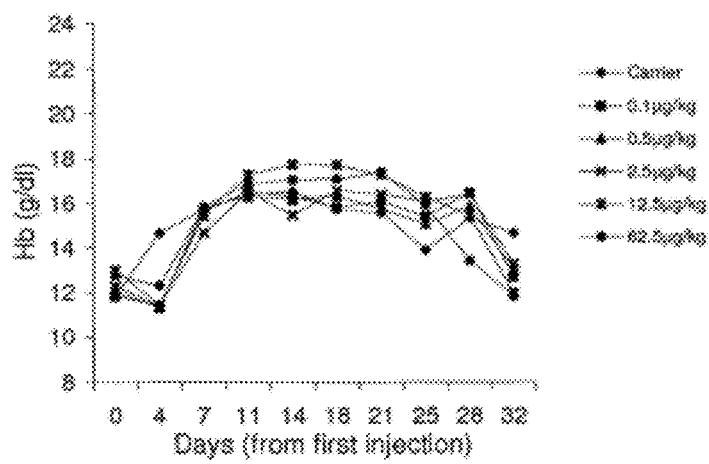
Figure 7

8A
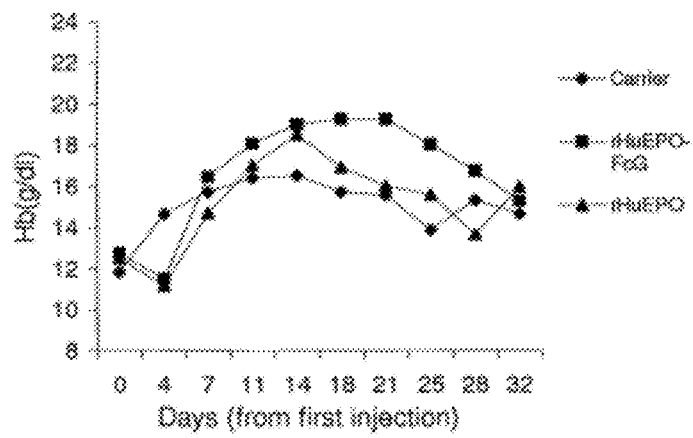
8B
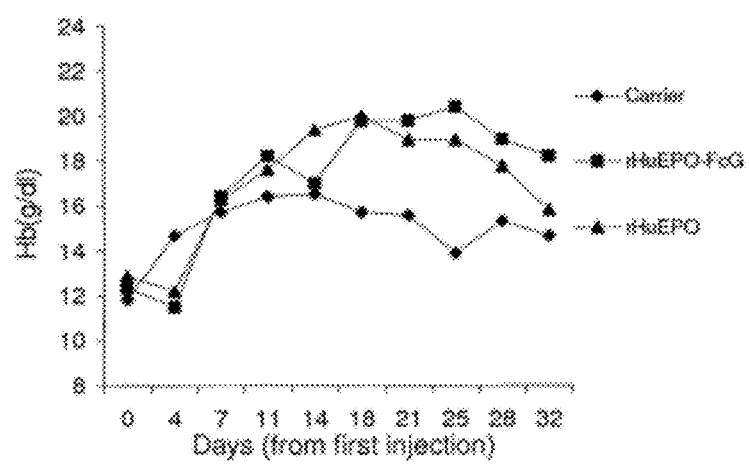
Figure 8

FUSION PROTEINS HAVING MUTATED IMMUNOGLOBULIN HINGE REGION

CROSS REFERENCE TO RELATED APPLICATIONS

This application is a continuation of U.S. patent application Ser. No. 12/180,455 filed 25 Jul. 2008, now issued as U.S. Pat. No. 8,067,548, which claims the benefit of U.S. Provisional Patent Application No. 60/952,181 filed 26 Jul. 2007. The disclosure of each of the previously referenced patent application(s) and patent(s) is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 700171_403C1_SEQUENCE LISTING.txt. The text file is 19.6 KB, was created on Aug. 2, 2017, and is being submitted electronically via EFS-Web.

TECHNICAL FIELD

This application relates to fusion proteins.

BACKGROUND

Recombinant human proteins corresponding to their natural amino acid sequences have been used for the treatment and diagnosis of a broad range of human diseases since the 1980s. However, most recombinant human proteins do not survive long enough in vivo and are rapidly cleared from circulation. For example, proteins with a molecular mass less than 20 kDa have been reported to be filtered at the level of renal tubules, often leading to a dose-dependent nephrotoxicity. The short in vivo half-life of these proteins compromises their natural biological functions, requiring higher doses or more frequent administration, which in turn impairs patient compliance and increases the burden on health care providers. These clinical demands merit the search and development of therapeutic proteins with longer circulation half-life.

In addition to the direct mutations of individual protein structure for achieving longer half-life (e.g. ARANESP™ by Amgen and TNKnase by Genentech), two systemic approaches have been used for the creation of therapeutic proteins with longer half-life. One is "PEGylation", which refers to chemical cross-linking of polyethylene glycol (PEG) compounds to target proteins. PEG-bound proteins have larger molecular sizes and are more slowly cleared from the circulation. PEGylation has been clinically demonstrated and recognized by the biotech industry as a standard method of extending the half-life of various target proteins. A shortcoming of PEGylation is the significant impairment of the biological activity of target proteins. The altered structure of PEGylated proteins also risks generating an immunogenic response in the human body.

Another systemic approach is the genetic fusion of target therapeutic protein(s) with another human carrier protein to stabilize the target protein in circulation in the form of a fusion protein complex. Two ideal human carrier protein candidates for fusion with therapeutic proteins are human immunoglobulin and albumin. Both immunoglobulin and albumin are very stable and abundant in blood. Fusion proteins comprising a therapeutic protein and either immunoglobulin or albumin would theoretically retain the biological activity of the therapeutic protein, be more stable in circulation than the therapeutic protein alone, and be completely homologous to natural human proteins, minimizing the risk of immunogenic responses [1, 2].

One practical strategy with this approach is to genetically fuse a therapeutic protein with an Fc fragment of a human immunoglobulin [1, 3, 4]. Modern bioengineering technology has successfully created fusion proteins consisting of a therapeutic protein, such as cytokines and soluble receptors, and an Fc fragment of immunoglobulin G (IgG) [5-26]. For example, IL-10, an anti-inflammatory and anti-rejection agent, has been fused to the N-terminal of murine Fc.gamma.2a to increase IL-10's short circulating half-life [9]. In another example, the N-terminal of human IL-2 has been fused to the Fc portion of human IgG 1 or IgG 3 to overcome the short half life of IL-2 and its systemic toxicity [26]. Two fusion proteins comprising an Fc fragment have been successfully developed as biomedicines and approved by FDA for the treatment of rheumatoid arthritis and chronic plaque psoriasis [27, 28, 29].

Human IgG is composed of four polypeptides (two identical copies of light chain and heavy chain) covalently linked by disulfide bonds. The proteolysis of IgG by papain generates two Fab fragments and one Fc fragment. The Fc fragment consists of two polypeptides linked by disulfide bonds. Each polypeptide, from the N-terminal to C-terminal, is composed of a hinge region, a CH2 domain and a CH3 domain. The structure of the Fc fragment is nearly identical across all subtypes of human immunoglobulin. IgG is one of the most abundant proteins in the human blood and makes up 70 to 75% of the total immunoglobulin in human serum. The half-life of IgG in circulation is the longest among all five types of immunoglobulin and may reach 21 days.

Disulfide bonds formed between thiol groups of cysteine residues play an important role in the folding and stability of proteins, usually when proteins are secreted to an extracellular medium. The disulfide bond stabilizes the folded form of a protein in several ways. First, it holds two portions of the protein together, biasing the protein towards the folded state. Second, the disulfide bond may form the nucleus of a hydrophobic core of the folded protein, i.e., local hydrophobic residues may condense around the disulfide bond and onto each other through hydrophobic interactions. Third, and related to the first and second points, by linking two segments of the protein chain and increasing the effective local concentration of protein residues, the effective local concentration of water molecules is lowered. Since water molecules attack amide-amide hydrogen bonds and break up secondary structures, disulfide bonds stabilize secondary structure in their vicinity. For example, researchers have identified several pairs of peptides that are unstructured in isolation, but adopt stable secondary and tertiary structure upon forming a disulfide bond between them. The native form of a protein is usually a single disulfide species, although some proteins may cycle between a few disulfide states as part of their function. In proteins with more than two cysteines, non-native disulfide species, which are almost always unfolded, may be formed.

A flexible junction region of the fusion protein which allows the two ends of the molecule to move independently plays a very important role in retaining each of the two moieties' functions separate and efficient. Therefore, the junction region should act as a linker which combines the two parts together, and as a spacer which allows each of the two parts to form its own biological structure and not interfere with the other part. Furthermore, in order to avoid the induction of immunogenicity, the junction region should be native to the human body and simple in structure [5, 25].

The primary structure of the hinge region of immunoglobulin includes three cysteines, such as $cys^{223}$, $cys^{229}$ and $cys^{232}$ in the case of the human IgG 1 structure used by the present inventors. While the $cys^{229}$ and $cys^{232}$ foam two interchain disulfide bonds by binding between counterparts of the two chains, the $cys^{223}$ remains free. Therefore, it is highly possible that this free cysteine may bind with another intrachain or interchain cysteine, to form a non-native disulfide bond in the protein maturation process upon secretion from host cells or during subsequent purification. This non-native disulfide bond may not only alter the structure and conformation of the therapeutic protein, but may also interfere with the biological activity of the therapeutic protein or induce harmful immunogenicity when the fusion protein is administered into the human body.

Many therapeutic proteins such as erythropoietin (EPO) and granulocyte macrophage colony-stimulating factor (GM-CSF) have a cysteine near their C-terminal. The role of this cysteine in maintaining proper structure and function has yet to be well-defined. The cysteine proximal to the C-terminal may be essential for maintaining proper structure, facilitating correct folding or retaining normal biological activity. The inventors hypothesize that if proteins with a cysteine near its C-terminal are fused to the natural sequence of the hinge region of a Fc fragment, the very limited space between the last cysteine of the C-terminal of the fused protein and the first cysteine of the N-terminal of the Fc fragment ($cys^{223}$) may lead to the formation of an unexpected disulfide bond between these two cysteines. The formation of the unexpected disulfide bond may alter the structure and/or the folding of the fused protein component as well as alter the flexibility of the hinge region. As a result, normal functions of the fused therapeutic protein in the fusion protein complex may be impaired.

Even if the target therapeutic protein does not contain a cysteine near its C-terminal, another cysteine in its structure may, after three dimensional folding, become sufficiently close to the free cysteine (e.g. $cys^{223}$) of the hinge region to form a non-natural disulfide bond that may alter the structure and biological activity of the fused target protein. The inventors' hypothesis may partially explain why there has yet to be any clinically-proven success in attempts to create functional fusion proteins with widely-used growth factors such as EPO, G-CSF and GM-CSF, etc.

Previous reports have used various methods to create fusion proteins between a therapeutic protein and an Fc fragment/immunoglobulin molecule. In most of these reports, researchers changed amino acid sequences of the target protein, added a linker peptide between the C-terminal of the target protein and the N-terminal of the hinge region of Fc fragment, or truncated the hinge region of the Fc fragment of the hinge region (resulting in the removal of the free cysteine (e.g. $cys^{223}$)).

In U.S. Pat. No. 5,908,626, a fusion protein of IFN β with a human immunoglobulin Fc fragment is described which was linked by a synthetic oligopeptide $(GGS)_2(GGGS)_2$ [SEQ ID NO: 17] [6]. The inventors in that patent believe this linker can "reduce the possibility of generating a new immunogenic epitope (a neoantigen) at what would otherwise be the fusion point of the IFN β and the immunoglobulin Fc fragment". In U.S. Pat. Nos. 6,797,493, 6,900,292, 7,030,226, 7,226,759, and 7,232,668, the hinge region was replaced by a 16-amino acid peptide linker $GS(GGGS)_3GS$ [SEQ ID NO: 18] [10, 12, 13, 20, 21]. In addition to the genetic approach, chemical manipulation has also been used to address the problem of non-native disulfide bonds. For example, the inventors in U.S. Pat. No. 6,808,902 developed a process for treating an IL-1ra-Fc fusion protein with a copper (II) halide in order to prevent or correct a non-native disulfide bond which caused misfolding of that fusion protein [12]. An Fc-EPO fusion protein (rather than the conventional EPO-Fc fusion) has shown poor pharmacokinetics and little EPO efficacy in mice; mutation of four amino acids of the EPO molecule is required to obtain a functional Fc-EPO fusion protein [30].

As mentioned above, the hinge region plays the role of the flexible junction region between the fused therapeutic protein and the Fc fragment (CH2 and CH3). Truncation or significant changes of the hinge region may have undesirable effects on ability of the hinge region to act as flexible junction. The addition of peptide linkers may not only impair the natural conformation of the fusion protein but also greatly increase the risk of immunogenecity by introducing a non-native structure.

The need exists for therapeutic protein/Fc fragment fusion proteins that have a prolonged half-life and/or enhanced activity without increasing the risk of an immunogenic response.

SUMMARY OF THE INVENTION

According to one aspect of the present invention, a fusion protein having a non-immunoglobulin polypeptide having a cysteine residue proximal to the C terminal thereof, and an immunoglobulin component with a mutated hinge region is provided. The mutation comprises a point mutated site corresponding in position to the position in a native hinge region of the cysteine residue located nearest the cysteine residue of the non-Ig component. The distance from the cysteine residue of the non-immunoglobulin polypeptide and any remaining cysteine residues of the mutated hinge region is sufficient to prevent the formation of a disulphide bond therebetween.

According to one aspect of the present invention a fusion protein having a non-immunoglobulin polypeptide and an immunoglobulin component is provided. The immunoglobulin component has a mutated hinge region. The mutation comprises a point mutated site in a hinge region of the immunoglobulin component promixate to the non-immunoglobulin polypeptide. A cysteine residue of the hinge region is substituted by a non-cysteine residue.

According to one aspect of the present invention, a fusion protein having a non-immunoglobulin polypeptide directly linked to a human immunoglobulin component is provided. The fusion protein has a prolonged half-life in vivo in comparison to naturally occurring or recombinant native non-immunoglobulin polypeptide.

According to one aspect of the invention, multimeric proteins comprising a plurality of the fusion proteins according to the foregoing aspects of the invention are provided.

According to one aspect of the invention, methods of producing fusion proteins according to the foregoing aspects of the invention are provided. The methods include the step of culturing a cell line transfected with a DNA molecule that encodes the sequence of the fusion protein and purifying the encoded protein.

According to one aspect of the invention, methods of stimulating white blood cell production in a mammal are provided, wherein the methods include the step of administering to the mammal a fusion protein according to the foregoing aspects of the invention.

According to one aspect of the invention, pharmaceutical compositions including a fusion protein according to the foregoing aspects of the invention and a pharmaceutically acceptable carrier, adjuvant or diluent are provided.

According to one aspect of the invention, methods of stimulating white blood cell production in a mammal are provided, wherein the methods include the step of administering to the mammal a pharmaceutical composition according to foregoing aspects of the invention.

BRIEF DESCRIPTION OF THE DRAWINGS

In drawings intended to illustrate various embodiments of the invention but which are not intended to be constructed in a limiting manner.

FIG. 2A is a schematic diagram showing the general structure of the DNA molecule encoding the recombinant human EPO-FcG fusion protein (rHuEPO-FcG) in which the first cysteine from the N-terminal of the hinge region ($cys^{223}$) is substituted by glycine and used as the mutant hinge region for the construction of an EPO-Fc fusion protein. This mutant hinge region-containing Fc fragment is referred to as FcG, and the Fc fragment containing the hinge region with the native cysteine at the sixth residue from its N-terminal as FcC respectively.

FIG. 2B is a sequence listing showing the nucleotide sequence [SEQ ID NO:1] and the deduced amino acid (aa) sequence [SEQ ID NO:2] of rHuEPO-FcG protein. The total length of DNA is 1281 bp. The 426 amino acids in the deduced protein sequence include 27 aa for the signal peptide and 399 aa for the complete rHuEPO-FcG protein. The complete rHuEPO-FcG protein consists of human EPO domain (166 aa), hinge region (16 aa, underlined), and CH2 and CH3 domains (217 aa) of the Fc fragment of human IgG1. The calculated molecular weight of the polypeptide of the mature rHuRPO-FcG fusion protein is 44.6 kDa, composed of 18.5 kDa (41.4%) of EPO fragment and 26.1 kDa (58.6%) of IgG 1 Fc fragment. A homodimer is formed by two disulfide bonds via the two cysteine residues (boxed) within the hinge region. At residue 172 of the mature fusion protein (i.e. the $6^{th}$ amino acid of hinge region) the native cysteine residue has been substituted by glycine (bold).

FIGS. 6A and 6B are graphs showing the dose-dependent increase of hemoglobin (Hb) levels in normal mice treated three times per week with a subcutaneous injection (s.c.) of rHuEPO-FcG or rHuEPO. Each point represents the mean Hb level of the group (6 mice). Day 0 levels represent the Hb levels before treatment. A: Mice treated with rHuEPO-FcG. B: Mice treated with native rHuEPO.

FIGS. 7A and 7B are graphs showing the dose-dependent increase of hemoglobin (Hb) levels in normal mice treated with once per week s.c. of rHuEPO-FcG or rHuEPO. Each point represents the mean Hb level of the group (6 mice). Day 0 levels represent the Hb levels before treatment. A: Mice treated with rHuEPO-FcG. B: Mice treated with native rHuEPO.

FIGS. 8A and 8B are graphs showing the increase of hemoglobin (Hb) levels in normal mice treated with intravenously injection (i.v.) of 12.5 µg/kg of rHuEPO-FcG or rHuEPO. Each point represents the mean Hb level of the group (6 mice). Day 0 levels represent the Hb levels before treatment. A: Mice with treatment once a week. B: Mice with treatment 3 times a week.

DETAILED DESCRIPTION OF THE INVENTION

Figure 1:
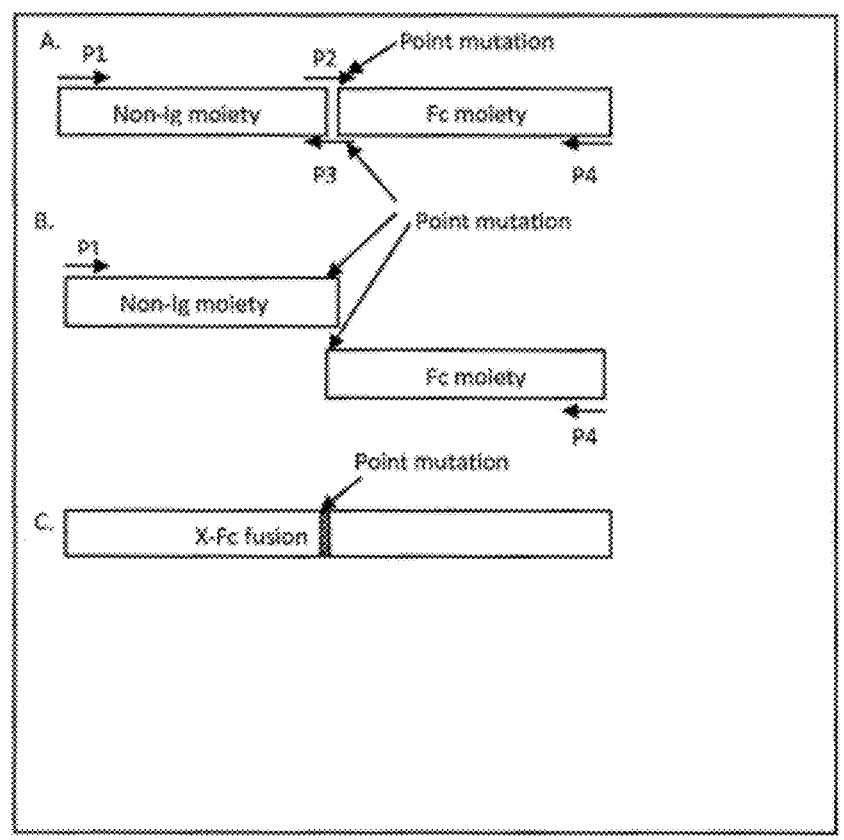
FIGS. 1A to 1C are schematic diagrams illustrating the strategy for generating point mutations and the amplification of the mutated whole gene encoding a Fc fusion protein simultaneously by overlapping PCR. A: A base-pair mutation was introduced into primers P2 and P3. The overlapping fragments of non-Ig and Fc with the desired mutation were amplified by p1/p3 and p2/p4 respectively. B: The mixed fragments from A served as a template. The whole molecule with the desired mutation was amplified by p1/p4. C: The resulting whole molecule with the desired mutation. X represents the non-Ig moiety of fusion protein.
Figure 3:
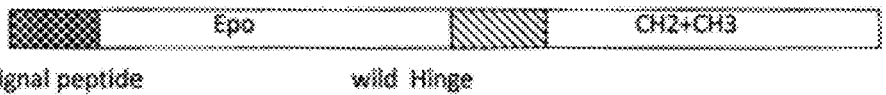
FIG. 3A is a schematic diagram showing the general structure of the DNA molecule encoding the wild type human EPO-FcC fusion protein (rHuEPO-FcC) in which the first cysteine from the N-terminal of the hinge region ($cys^{223}$) is maintained.
FIG. 3B is a sequence listing showing the nucleotide sequence [SEQ ID NO:3] and the deduced amino acid (aa) sequence [SEQ ID NO:4] of a wild type rHuEPO-FcC protein. The sequence particulars are the same as shown in FIG. 2B except that the native, wild type cysteine residue is maintained at residue 172 of the mature fusion protein (i.e. the $6^{th}$ amino acid of the hinge region).

Throughout the following description specific details are set forth in order to provide a more thorough understanding of the invention. However, the invention may be practiced without these particulars. In other instances, well known elements have not been shown or described in detail to avoid unnecessarily obscuring the present invention. Accordingly, the specification and drawings are to be regarded in an illustrative, rather than a restrictive sense.

This invention relates to recombinant human fusion proteins combining a target protein or polypeptide, such as a non-immunoglobulin polypeptide, with a Fc fragment or immunoglobulin molecule. The Fc fragment or Ig molecule includes a mutant hinge region wherein the first cysteine from the N-terminal of the hinge region (e.g. in human IgG 1, the sixth amino acid, cys$^{223}$) is replaced by a non-cysteine residue, such as a non-charged, non-polar amino acid (neutral amino acid). The result is a mutant hinge region which maintains the natural length and flexibility of the hinge region without the free cysteine that may lead to the formation of a non-natural disulfide bond with a cysteine in the non-immunoglobulin polypeptide. The mutant hinge region may comprise the whole or part of the human Fc fragment, or the whole or part of a human immunoglobulin molecule.

When any non-immunoglobulin polypeptide is directly fused to the hinge region of the Fc fragment or Ig molecule to form a protein-Fc or protein-Ig fusion protein, respectively, it is believed the mutant hinge region lacking the N-terminal free cysteine allows the fused target polypeptide to maintain its structure, folding and biological functions. In particular, it is believed that any cysteine residues proximal to the C terminal of the target non-immunoglobulin polypeptide are thus prevented from forming any unexpected disulphide bonds with the N-terminal free cysteine found in the native hinge region. Cysteine residues "proximal" to the C terminal of the non-immunoglobulin polypeptide include those proximal with reference to position along the amino acid chain and as well to those proximal as result of three-dimensional folding of the non-immunoglobulin polypeptide. The fusion proteins created with this mutant hinge region have near 100% sequence identity to natural sequences of both the target protein and hinge region, and therefore possess minimum immunogenecity risks.

The first cysteine from the N-terminal of the hinge region of human Fc fragment/immunoglobulin (e.g. the sixth amino acid, cys$^{223}$, in human IgG 1) may be substituted with any non-charged, non-polar amino acid (neutral amino acid). In the example disclosed herein, glycine was used to replace the free cysteine. A person skilled in the art would appreciate that other amino acids could also replace the free cysteine.

The mutant hinge region that is formed by substituting the free cysteine near its N-terminal as part of the Fc fragment or Ig molecule provides a method or platform for generically producing fusion proteins between any non-immunoglobulin polypeptide and Fc/Ig to prevent non-naturally occurring disulfide bonds, and thus retain the biological functions of the fused target polypeptide.

Several methods can be used to make the desired point mutation. One method, described in Example 1 of this invention, adopts overlapping PCR to amplify the whole nucleic acid sequence of the fusion protein. With specifically-designed oligo primers, the desired point-mutation can be introduced into the resulting nucleic acid sequence following gene amplification. Other methods, such as the Quick-Change™ mutagenesis method from Invitrogen or artificial gene synthesis can also be used to produce the point mutation. A person skilled in the art would appreciate that any number of different methods could be used to substitute the free cysteine of the hinge region (e.g. cys$^{223}$).

The fusion protein created by using the mutant hinge region according to an embodiment of the present invention comprises a non-Ig moiety linked to an Fc fragment of IgG expressed by the formula "X-hinge region-CH2-CH3", wherein X represents the non-Ig moiety, and CH2 and CH3 represent two heavy chain domains of the Fc fragment of IgG.

The hinge region refers to the region between the CH1 and CH2 heavy chain domains that contains the inter-chain disulfide bonds. Flexibility in this region allows the molecules on both sides of the hinge region to move independently. The heavy chains are also glycosylated in this region, which helps protect this relatively exposed area against degradation. In one embodiment, the non-Ig moiety of the fusion protein links to the hinge region directly, i.e. the C-terminal of the non-Ig moiety is directly fused to the N-terminal of hinge region. The first cysteine (e.g. cys$^{223}$) from the N-terminal of the hinge region may be substituted by a non-charged, non-polar amino acid, such as glycine. In some embodiments, a synthetic linker, such as (G4S)3 [SEQ ID NO: 19] or G4SG5S [SEQ ID NO: 20], may be inserted between the non-Ig moiety and Fc fragment to ensure each part folds properly. In other embodiments, one or more of the amino acid residues upstream of the first cysteine (e.g. cys$^{223}$) site may be removed.

The non-immunoglobulin polypeptide may be, but is not limited to, any peptide or polypeptide sequence with human or non-human origin, having complete or non-complete amino acid sequences corresponding to any defined human and non-human proteins, exhibiting biological functions or non-biological functions, made artificially or obtained naturally. The non-immunoglobulin polypeptide may also be a variant of any proteins defined or non-defined before. These variants include but are not limited to polypeptide sequences modified from a native protein sequence but still partially or completely retaining its biological functions. Modifications include but are not limited to substitution, addition, insertion, deletion, or rearrangement of the amino acids of the native polypeptide sequences.

The non-immunoglobulin polypeptide may, for example, be a cytokine. "Cytokine" is used herein to describe proteins, analogs thereof, and fragments thereof which are produced by and excreted from a cell, and which elicit the biological response by binding with corresponding receptors. Cytokines include but are not limited to hematopoietic factors such as EPO, GM-CSF and granulocyte colony stimulating factor (G-CSF), interferons such as IFN α, IFN β and IFN γ, interleukins such as IL-2, IL-4, IL-5, IL-6, IL-7, IL-10, IL-11, IL-13, IL-14, IL-15, IL-16 and IL-18, tumor necrosis factors such as TNF α, and lymphokines such as lymphotoxin.

The non-immunoglobulin polypeptide may also be a ligand-binding protein that may block a receptor-ligand interaction at the cell surface, or neutralize the biological activity of another molecule in the body fluids. Ligand-binding proteins include but are not limited to CDs molecules, CTLA-4, TNF receptors, and interleukin receptors.

The non-immunoglobulin polypeptide may also be a hormone, a neurotrophin, a neutrophin receptor (e.g. Trk A), a body-weight regulator, a serum protein, a clotting factor, a protease, an extracellular matrix component, an angiogenic factor, an anti-angiogenic factor, an immunoglobulin receptor (e.g. IgG receptor), a blood factor (e.g. Factor VIII, Factor IX, Factor X), a cancer antigen (e.g. PSA, PSMA), a statin (e.g. endostatin, angiostatin) a therapeutic peptide or a growth-factor (e.g. Flt-3).

The non-immunoglobulin polypeptide may also be a non-human or non-mammalian protein, or even a protein toxin. Examples include gp120, HIV transactivators, surface proteins from other viruses such as HBV, HCV and RSV, and parasitic surface proteins such as malarial antigens.

A recombinant vector with the nucleic acid sequence encoding the Fc fragment containing a mutant hinge region may be constructed. This vector, which possesses all the elements needed for its propagation, selection, and screening in either prokaryotic cells (such as E. coli) or eukaryotic cells (such as CHO cells), can serve as a platform to express Fc fusion proteins described in this invention. By using this platform, the nucleic acid sequence encoding the non-Ig moiety of the fusion protein is conveniently inserted in-frame into the vector at the 5'-end of nucleic acid sequence encoding the mutated Fc moiety by molecular cloning techniques.

As a specific example, a novel fusion protein having enhanced erythropoietic properties was produced according to the present invention. The fusion protein, referred to herein as rHuEPO-FcG, comprises a human EPO molecule genetically linked to an immunoglobulin Fc fragment containing a mutant hinge region of the present invention. The nucleic acid sequence of the rHuEPO-FcG fusion protein of the present invention is shown in SEQ ID No: 1, and the corresponding deduced amino acid sequence is shown in SEQ ID No: 2. As discussed further below, the fusion protein may be in the form of a dimer comprising two identical polypeptide subunits. Each polypeptide subunit, from the N-terminal to C-terminal, includes the polypeptide sequence of the human EPO molecule, and the polypeptide sequence of the hinge region, CH2 domain and CH3 domains of the Fc fragment of human immunoglobulin IgG 1. The two polypeptide subunits are joined by disulfide bonds between the respective hinge regions to form the dimer structure. The dimer has the same general shape as an IgG molecule and exhibits better stability than free EPO molecules as demonstrated in the examples below.

As will be apparent to a person skilled in the art, the hinge region of an intact immunoglobulin provides the protein sufficient flexibility for effective antigen-antibody binding. Similarly, in the present invention, the hinge region in which the free cysteine (e.g. cys$^{223}$) is substituted by glycine is included in the design of the rHuEPO-FcG fusion protein to maintain its flexibility, particularly when the fusion protein is in the dimer form. As described below, this likely allows the normal binding of the EPO portion of the rHuEPO-FcG fusion protein to EPO receptors to effect the biological functions of EPO. It is believed that the dimer form of the rHuEPO-FcG fusion protein, by providing two EPO molecules, is capable of inducing optimal activation of EPO receptors (for example, by facilitating receptor cross-linking).

As demonstrated in the examples set forth below, the rHuEPO-FcG fusion protein has been successfully synthesized using recombinant DNA techniques. The fusion protein has been shown in mice, rat and primate studies to exhibit a prolonged in vivo half-life and enhanced erythropoietic properties in comparison to naturally occurring or recombinant native human EPO. The rHuEPO-FcG fusion protein containing the mutant hinge region exhibits normal or even enhanced erythropoietic functions in normal animals and animals with experimental anemia. The half-life of this fusion protein in circulation in primate studies reached 37 hours in comparison to 8 hours for native human erythropoietin and 24 hours for ARANESP from Amgen. As used in this patent application, the terms "native human erythropoietin" and "native human EPO" mean EPO having an identical and complete amino acid sequence of the wild type EPO molecule. As will be appreciated by a person skilled in the art, native human EPO may be naturally occurring or recombinantly produced (e.g. rHuEPO alpha). The term "native human EPO" does not include rHuEPO analogs, such as darbepoetin alpha where the EPO structure has been significantly modified, such as by hyperglycosylation.

The nucleic acid sequence of the rHuEPO-FcG fusion protein of the present invention is shown in FIG. 2B. The complete rHuEPO-FcG fusion protein is 399 amino acids in length. As shown in FIG. 2B, the complete rHuEPO-FcG fusion protein consists of the EPO domain (166 amino acids), the hinge region (16 amino acids, underlined) and the CH2 and CH3 domains (217 amino acids). A signal or leader peptide sequence consisting of 27 amino acids is also shown in FIG. 1B. The signal peptide is cleaved during synthesis of rHuEPO-FcG.

As shown best in FIG. 2B, the EPO domain has a cysteine residue near its C-terminal (amino acid number 161). The mutant hinge region includes 2 cysteine residues, at amino acid numbers 178 and 181 which are boxed in FIG. 2B. The hinge region cysteine residues form the disulphide bonds between the polypeptide subunits of the homodimer as discussed above. The naturally occurring hinge region of a human IgG 1 fragment also has a cysteine at residue number 6 of the hinge region portion (measured from the N-terminal). According to an embodiment of the present invention, the cysteine residue 6 of the hinge portion has been substituted by a non-cysteine residue. In particular, in the embodiment of FIG. 2B, the cysteine has been substituted by glycine (at amino acid residue 172 of rHuEPO-FcG, which corresponds to residue 6 of the hinge region). As will be apparent to a person skilled in the art, other non-cysteine residues could also be substituted for cysteine at this location to avoid formation of a disulfide bond.

As a result of the amino acid substitution at residue 172, the first cysteine residue of the hinge region (at residue 178) is spaced 17 amino acids from the above-described cysteine residue of the EPO domain (at residue 161). The inventors believe that the minimum spacing between the cysteine residue 161 of the EPO domain and the first cysteine residue of the hinge region should be at least 12 amino acids to enable successful assembly and/or EPO receptor binding of a homodimer of rHuEPO-FcG. That is, if residue 172 is a cysteine residue, an undesirable disulfide bond may potentially be formed, such as between cysteine residues 161 and 172. This may alter the three dimensional structure of the EPO molecule, resulting in the impairment and/or the loss of the biological functions of EPO.

In one embodiment of the invention, the EPO domain is linked directly to the Fc fragment portion of the fusion protein. By avoiding an external linker peptide, the preferred three dimensional structure of the rHuEPO-FcG fusion protein is maintained and the risk of triggering an undesirable immunogenic response is minimized. The hinge region of the Fc fragment is preferably at least 9 amino acids in length and is preferably in the range of about 10 to 20 amino acids in length.

As another specific example, a fusion protein combining human GM-CSF and the mutated Fc fragment was also produced genetically (rHuGMCSF-FcG). The nucleic acid sequence of the rHuGMCSF-FcG fusion protein of the present invention is shown in SEQ ID No: 5. The corresponding deduced amino acid sequence is shown in SEQ ID No: 6. In vivo experiments in animals with experimental neutropenia demonstrate that rHuGMCSF-FcG exhibits enhanced biological functions in twills of stimulating the growth of white blood cells (WBC) as compared to rHuGMCSF.

Accordingly, two fusion proteins formed by direct linking of the target proteins, human EPO and GM-CSF, to the mutant hinge region in which the free cysteine (e.g. the sixth amino acid, $cys^{223}$, in human IgG 1) was substituted by glycine, showed at least full biological functions of the fused target proteins, as compared to their natural molecules. These results strongly suggest that the mutant hinge region of the present invention allows the direct fusion of a target protein to an Fc fragment/Ig molecule while retaining biological functions of the fused target protein. The resulting fusion protein of target protein-Fc/Ig complex, in addition to retaining natural biologic functions, exhibits significantly prolonged half-life in vivo.

In a further embodiment, the mutant hinge region without the free cysteine (e.g. the sixth amino acid, $cys^{223}$, in human IgG 1) could be used as a standard platform for generating fusion proteins that have longer circulation half-life and/or exhibit full or enhanced biological functions compared to the target protein. Unlike PEGylation, an advantage of making fusion proteins of the present invented is that the biological activity of the target protein will not be impaired and the potential immunogenic responses are minimized since the fusion protein has almost 100% sequence identity to natural human proteins (i.e., only one amino acid is different).

EXAMPLES

The following examples will further illustrate the invention in greater detail although it will be appreciated that the invention is not limited to the specific examples.

1. Generation and Amplification of Mutated Nucleic Acid Sequences Encoding the Fusion Proteins rHuEPO-FcG and rHuGMCSF-FcG Full length DNA molecules encoding the amino-acid sequence of the polypeptide of rHuEPO-FcG, rHuEPI-FcC (wild type) and rHuGMCSF-FcG were generated by overlapping PCR using the following oligo primers (QIAGEN Inc., US), respectively:

[SEQ ID NO: 7]
EF5:   5'-ccggaattcgccaccatgggggtgcacgaatgtcctgcct-3'

[SEQ ID NO: 8]
EF3:   5'-ttttccttttgcggccgcttatttacccggagacagggagag-3'

[SEQ ID NO: 9]
EFL5:  5'-aggcctgcaggacaggggacagagttgagcccaaatctggtgaca-3'

[SEQ ID NO: 10]
EFL3:  5'-tgtcaccagatttgggctcaactctgtccctgtcctgcaggcct-3'

[SEQ ID NO: 11]
EFL5w: 5'-aggcctgcaggacaggggacagagttgagcccaaatcttgtgaca-3'

-continued

```
                                                            [SEQ ID NO: 12]
EFL3w:  5'-tgtcacaagatttgggctcaactctgtccctgtcctgcaggcct-3'

[SEQ ID NO: 13]
GF5:    5'-actgaattcgccaccatgtggctgcagagcctgctgctcttgggcactgtggcctgc-3'

[SEQ ID NO: 14]
GF3:    5'-ttttccttttgcggccgcttatttacccggagacagggagag-3'

[SEQ ID NO: 15]
GFL5:   5'-gactgctgggagccagtccaggaggttgagcccaaatctggtgacaaaac-3'

[SEQ ID NO: 16]
GFL3:   5'-gttttgtcaccagatttgggctcaacctcctggactggctcccagcagtc-3'
```

An EcoR I site was introduced in EF5 and GF5, and a Not I site was introduced in EF3 and GF3. For optimal expression of the proteins in mammalian cells, the Kozak sequence (GCCACCATGG) [SEQ ID NO: 21] was also introduced in EF5 and GF5. The pairs EFL5/EFL3 and EFL3w/EFL5w are complementary sequences consisting of the 3'-terminal DNA sequence of EPO (23 bp) and the 5'-terminal DNA sequence of mutated and wild IgG 1 hinge (22 bp), respectively. The pair of GFL5/GFL3 are complementary sequences consisting of the 3'-terminal DNA sequence of GM-CSF (24 bp) and the 5'-terminal DNA sequence of mutated IgG 1 hinge (26 bp).

A. Generation of Wild and Mutated Sequences of rHuEPO-FcG

First, an EPO DNA fragment of 0.6 kb was amplified by PCR (Platinum Taq DNA Polymerase High Fidelity) with primers EF5 and EFL3 or EFL3w from plasmid p9E containing the full length of human EPO cDNA, mutated and wild Fc fragment of 0.7 kb with primers EF3/EFL5, and EF3/EFL5w from plasmid pD containing the full length of human IgG1 cDNA sequence, respectively (p9E and pD are from the inventors' own lab). The two fragments were then purified and mixed in equal amount. Using the mix as a template, the full length mutated and wild rHuEPO-FcG DNA of 1.3 kb was amplified by primers EF5 and EF3, respectively.

B. Generation of Mutated Sequence of rHuGMCSF-FcG

First, a GM-CSF DNA fragment of 0.4 kb was amplified by PCR (Platinum Taq DNA Polymerase High Fidelity) with primers GF5 and GFL3 from plasmid pSS-GM containing the full length of human GMCSF cDNA, and a mutated Fc fragment of 0.7 kb was amplified with primers GF3/GFL5 from plasmid pD containing the full length of human IgG1 cDNA sequence (pSS-GM and pD are from the inventors' own lab). The two fragments were then purified and mixed in equal amount. Using the mix as a template, the full length of mutated rHuGMCSF-FcG DNA of 1.1 kb was amplified by primers GF5 and GF3.

2. Construction of the Recombinant Plasmids

Recombinant plasmids pCdEpo-FcG, pCdEpo-FcC and pCdGMCSF-FcG encoding the fusion protein of rHuEPO-FcG, rHuEPO-FcC and rHuGMCSF-FcG, respectively, were constructed by cloning the amplified nucleic acid sequences from Example 1 into expression vector pCD1.

The purified three fragments were digested by EocR I and Not I (New England Biolab Inc., USA) and then cloned into EcoR I/Not I-digested mammalian expression vector pCD1 (FIG. 2). The resulting recombinant vectors were named pCdEpo-FcG, pCdEpo-FcC and pCdGMCSF-FcG. The inserted nucleic acid sequences encoding the amino-acid sequence of the rHuEPO-FcG, rHuEPO-FcC and rHuGMCSF-FcG were confirmed by DNA sequencing.

3. Establishment of rHuEPO-FcG, rHuEPO-FcC, and rHuGMCSF-FcG Expression Cell Lines Chinese hamster ovary (CHO) cells with dihydrofolate reductase (dhfr) deficiency (CHO/dhfr⁻, ATCC No. CRL-9096), which have been approved by the FDA for biological substance production, were used as host cells for recombinant expression of rHuEPO-FcG, rHuEPO-FcC, and rHuGMCSF-FcG.

The CHO-dhfr⁻ cells were transfected with the recombinant vectors pCdEpo-FcG, pCdEpo-FcC and pCdGMCSF-FcG using Lipofectamine (Gibco, Cat. No: 18292-037, USA). The supernatants from the culture of selected clones were assayed by ELISA (Roche, Cat. No: 1-693 417 and Cat. No: HSGMO, Canada) for EPO and GM-CSF activity respectively. Positive clones were further screened under increasing methotrexate (MTX) pressures. Cell lines with highest protein expression were selected, and gradually adapted to serum-free media (CD CHO Medium, Gibco, and Cat. No: 10743-029, USA). These selected CHO cell lines were used for the production of rHuEPO-FcG, rHuEPO-FcC, and rHuGMCSF-FcG, respectively.

4. Purification of rHuEPO-FcG, rHuEPO-FcC, and rHuGMCSF-FcG Proteins rHuEPO-FcG, rHuEPO-FcC, and rHuGMCSF-FcG protein molecules contained in the supernatants collected from the serum-free media culturing the selected CHO cells were isolated at first by Protein A affinity chromatography (Amersham, Cat. No: 17-0402-01, Canada). The isolated proteins were further purified by gel filtration in HiLoad 16/60 Superdex 200 pg columns (Amersham, Cat. No: 17-1069-01, Canada). The purity of the rHuEPO-FcG, rHuEPO-FcC, and rHuGMCSF-FcG proteins was more than 98% as determined by electrophoresis.

5. Determination of the Sizes of the Purified rHuEPO-FcG Protein

First, SDS-PAGE was carried out to determine the sizes of the purified rHuEPO-FcG, rHuEPO-FcC, and rHuGMCSF-FcG proteins. A single band with molecular weight of about 180 kDa for rHuEPO-FcG and rHuEPO-FcC, and 140 kDa for rHuGMCSF-FcG was seen on an 8% Bis-Tris gel under non-reducing conditions, which measures the overall size of the protein with the existence of disulfide bonds. This indicated that most of these recombinant protein molecules were produced in their dimeric form, as expected from the design of the fusion protein. When SDS-PAGE analysis was conducted under reducing conditions (100 mM dithiothreitol (DTT)) to break the disulfide bonds, only single bands with molecular weight of 75 kDa and 60 kDa were identified, consistent with the estimated molecular weight of single polypeptide chains of HuEPO-hinge region-CH2-CH3 and HuGMCSF-hinge region-CH2-CH3, respectively.

The molecular weight of the purified rHuEPO-FcG fusion protein with glycosylation was determined by mass spectrometry (MALDI-TOF-MS) to be 111099 daltons (111.1 kDa). In this assay, only a single peak of protein was observed, indicating that the purified rHuEPO-FcG protein was nearly 100% pure. The 15 amino acids of the N-terminal of the pure rHuEPO-FcG protein were determined by protein sequence analysis as: APPRLICDSRVLERY [SEQ ID NO: 22]. This was consistent with the sequence of the first 15 amino acids of the native human EPO polypeptide, and confirms that the purified rHuEPO-FcG G protein does have the correct and complete EPO molecule sequence as predicted by the DNA sequence encoding the amino acid sequences of the rHuEPO-FcG G fusion protein.

6. Enhanced Erythropoietic Activities of rHuEPO-FcG in Normal Mice

In vivo experiments in mice were conducted to confirm the retention of erythropoietic activity of the rHuEPO-FcG protein and to determine its efficacy compared to rHuEPO and darbepoetin-alpha. For comparison purposes, the doses of EPO used in the described animal experiments of the invention, namely rHuEPO-FcG, rHuEPO (i.e., native human EPO) and darbepoetin-alpha, were compared according to the amount of EPO molecule portion alone. In respect of rHuEPO-FcG protein, the EPO portion contributes to 41.4% of the total rHuEPO-FcG molecular weight as calculated by the ratio of the weight of amino acids of EPO to weight of the total amino acids of the whole rHuEPO-FcG molecule (166 of 399 amino acids). The EPO amount for rHuEPO-FcG was thus determined to be 41.4% of the total amount of rHuEPO-FcG protein.

rHuEPO-FcG (stock concentration: 0.5 mg/ml, purity of 98.6%) and native human rHuEPO (i.e. with natural human EPO structure) (6000 IU/0.5 ml, manufactured by Kirin Brewery Co., Japan) were diluted in carrier solution (2.5 mg/ml of human serum albumin, 5.8 mg/ml of sodium citrate, 0.06 mg/ml of citric acid and 5.8 mg/ml of sodium chloride, pH 5.5-5.6). The dose of rHuEPO was calculated according to its activity/amount ratio. BALB/c mice (6 to 8 weeks old, weighing 18-22 g, equal numbers of male and female, purchased from Experiment Animal Center, AMMS, China) were grouped randomly with 6 in each group. Each group of mice was treated with one combination of one dose (0.1, 0.5, 2.5, 12.5, 62.5 μg/kg), one injection route (i.v. through the tail vein or s.c.) and one injection schedule (three times per week or once per week). The control group of mice was injected with an equal volume of carrier solution. The treatment lasted for 3 weeks and the total observation time was 5 weeks. Peripheral blood samples (tail vein) were taken before treatment, on the 4$^{th}$ day and 7$^{th}$ day of every week for 5 weeks. Hemoglobin (Hb) was measured as the index by absorptiometry. Mean±SD was calculated from the data of each group and a t test was conducted among different groups.

Figure 4:
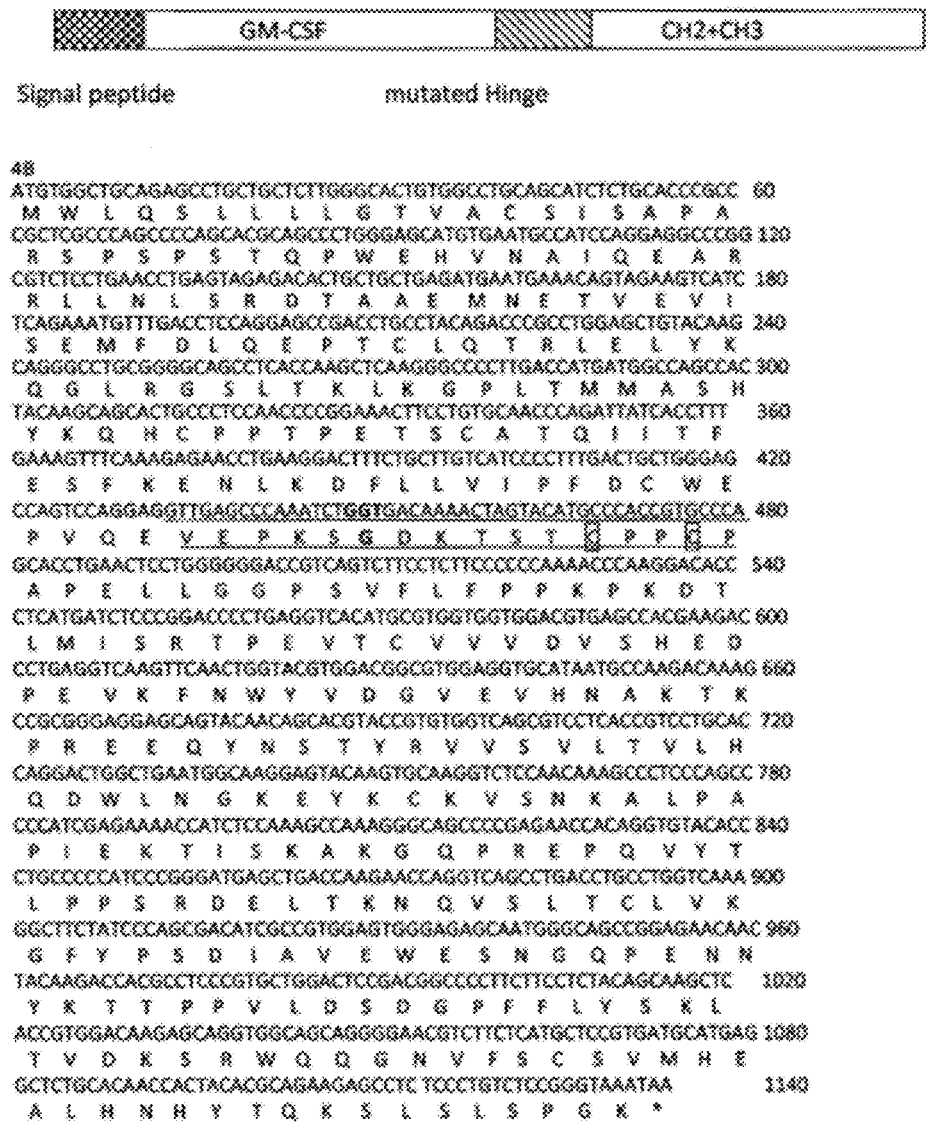
FIG. 4A is a schematic diagram showing the general structure of the DNA molecule encoding the fusion protein between native GM-CSF molecule and the FcG fragment (HuGMCSF-FcG).
FIG. 4B is a sequence listing showing the nucleotide sequence [SEQ ID NO:5] and the deduced amino acid (aa) sequence [SEQ ID NO:6] of rHuGMCSF-FcG fusion protein. The total length of DNA is 1131 bp. The 377 amino acids in the deduced protein sequence include 17 aa for the signal peptide and 360 aa for the complete HuGMCSF-FcG fusion protein. The complete rHuGMCSF-FcG fusion protein consists of complete GM-CSF molecule (127 aa), mutant hinge fragment (16 aa, underlined), and CH2 and CH3 domains (217 aa) of the Fc fragment of human IgG 1. The calculated molecular weight of mature rHuGMCSF-FcG fusion protein is 40.6 kDa, composed of 14.5 kDa (35.7%) of GM-CSF fragment and 26.1 kDa (64.3%) of IgG 1 Fc fragment. A homodimer is formed by two disulfide bonds via the two cysteine residues (boxed) within the hinge region. At residue 150 of the fusion protein (i.e. the $6^{th}$ amino acid of hinge region) the native cysteine residue has been substituted by glycine (bold).

The administration of EPO three times per week to mice, provided that the EPOs have normal erythropoietic activity, would induce saturated stimulation of erythropoiesis. As shown in FIG. 4, both groups treated 3 times per week s.c. had significant elevation of Hb levels even at the dose of 2.5 μg/kg. This experiment demonstrated that rHuEPO-FcG exhibited an in vivo erythropoietic activity as effective as rHuEPO. The elevation of Hb levels in the treated group was dose-dependent. However, saturated elevation of the Hb levels was induced in mice at the dose of 12.5 μg/kg of rHuEPO-FcG, whereas the similar saturated elevation of the Hb levels was only achieved at the dose of 62.5 μg/kg of rHuEPO. The elevation of Hb levels induced by 2.5 μg/kg of rHuEPO-FcG was also greater than that by 2.5 μg/kg of rHuEPO. These results suggest more potent erythropoietic stimulation by rHuEPO-FcG compared to rHuEPO.

Figure 5:
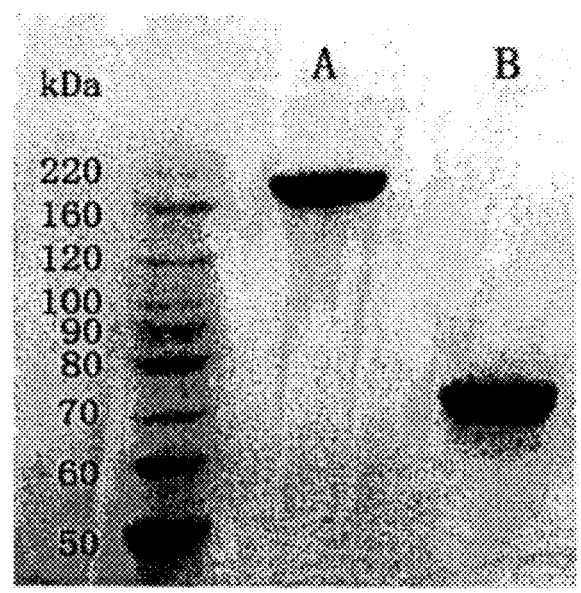
FIG. 5 is an image showing the sizes of the dimeric form of pure rHuEPO-FcG protein in non-reduced condition and monomeric form of pure rHuEPO-FcG protein in reduced condition by SDS-PAGE analysis. The purified rHuEPO-Fc protein from the supernatants of the cultured CHO cell-line expressing rHuEPO-FcG exists mainly as the dimeric form and has a molecular weight of about 180 kDa on 8% bis-tris gel in non-reduced condition. In reduced condition (100 mM dithiothreitol (DTT)) to break disulfide bonds, the dimer is separated into two identical monomeric units with a molecular weight of 75 kDa.

The erythropoietic potency of rHuEPO-FcG was further explored by reducing the injection times to once per week subcutaneously. As shown in FIG. 5, the rHuEPO-FcG-treated groups showed dose-dependent elevation of Hb levels at the doses of 12.5, or 62.5 μg/kg. Both doses of 12.5 and 62.5 μg/kg of rHuEPO also induced the elevation of Hb levels to a similar extent, which was much lower than that by 62.5 μg/kg of rHuEPO-FcG. This strongly indicates that rHuEPO-FcG has enhanced erythropoietic activity in vivo, presumably due to either the prolonged half-life of the rHuEPO-FcG in vivo or improved EPO receptor binding/activation by the dimer EPO molecules in the rHuEPO-FcG protein, or by the combined effects of both.

When the same doses (12.5 μg/kg) of rHuEPO-FcG or rHuEPO were administered intravenously either three times per week or once per week, elevation of the Hb levels was observed for all the treated groups (FIG. 6). However, i.v. administration once per week of rHuEPO-FcG induced greater, more persistent elevation of the Hb levels, which continued longer after the treatment was over. This data provides further support for the enhanced erythropoietic properties of the rHuEPO-FcG protein in comparison with rHuEPO having the structure of naturally occurring EPO protein.

7. Enhanced Erythropoietic Activities of rHuEPO-FcG in 5/6 Nephrectomized Rats

Experiments in normal mice proved the enhanced erythropoietic activities of rHuEPO-FcG in vivo. To further observe the efficacy of rHuEPO-FcG in stimulating erythropoiesis, pharmacodynamic studies were conducted in rats with experimental renal anemia induced by 5/6 nephrectomy. The efficacy of rHuEPO-FcG was compared with those of rHuEPO and darbepoetin-alpha (60 μg/ml, lot. No. N079, manufactured by Kirin Brewery Co., Japan).

Wistar rats (male and female in equal number, weighing 160-180 g, purchased from Vitalriver Experiment Animal Inc., Beijing, China. Licence No. SCXK11-00-0008) were used to create the anaemia model due to the renal functional failure by a two-step nephrectomy [27]. 5/6 nephrectomy was performed on rats with general anaesthesia by two separate operations under sterile conditions. After ⅔ of the left kidney was resected, the rats were allowed to recover for twenty days. The right kidney was then resected. Antibiotics were administered to prevent infection after each operation. In total, 5/6 of the kidney tissue from each rat was resected. The nephrectomized rats gradually developed renal function insufficiency and anaemia. Anaemia stabilized 50 days after the nephrectomy, and the rats were then randomly grouped (9 per group) to begin administration of the EPOs. Each group of rats was treated with one combination of one dose (2.5, 12.5, 62.5 μg/kg), one injection route (i.v. through the tail vein or s.c.) and one injection schedule (once per week or once every 2 weeks). The control group and model group of rats were injected with an equal volume of carrier solution. Treatment lasted for 4 weeks and the total observation time was 6 weeks.

All doses (2.5, 12.5, 62.5 μg/kg) of rHuEPO-FcG, administrated subcutaneously once per week, induced dose-dependent elevation of Hb levels compared to the model control group that did not receive EPO treatment. Both 12.5 and 62.5 μg/kg of rHuEPO or darbepoetin, administrated subcutaneously once per week also induced elevation of Hb levels. The increased levels of Hb in both groups treated with 12.5 or 62.5 μg/kg of rHuEPO-FcG were significantly higher than those in groups treated with 12.5 or 62.5 µg/kg of rHuEPO respectively. The Hb levels in 62.5 µg/kg of rHuEPO-FcG-treated group were also slightly higher than that in 62.5 µg/kg of darbepoetin-treated group. After stopping treatment, the decrease of Hb levels in the 62.5 µg/kg of rHuEPO-FcG-treated group was much slower and the Hb levels remained higher than those of both normal control and model control groups until the end of observation (two weeks after treatment), indicating a stronger and/or a prolonged erythopoietic stimulation (summarized in FIG. 7).

For treatment with subcutaneous injection once every two weeks, only 12.5 or 62.5 µg/kg of the three EPOs were administrated (FIG. 8). 12.5 µg/kg of rHuEPO barely increased Hb levels compared to the model control group, and the weak erythropoietic response in the 62.5 µg/kg of rHuEPO-treated group failed to bring the Hb levels to normal in comparison with the normal control group. Treatments of either rHuEPO-FcG or darbepoetin at the doses of 12.5 or 62.5 µg/kg induced significant elevation of Hb levels that was higher than that of the normal control group, indicating the effective correction of anaemia by both rHuEPO-FcG and darbepoetin. No significant differences were observed between same doses of rHuEPO-FcG and darbepoetin in terms of efficacy. The high dose of 62.5 µg/kg resulted in the persistent increase of erythropoiesis until the termination of the observation (two weeks post treatment). This further suggested that rHuEPO-FcG and darbepoetin exhibit the property of long-lasting stimulation of erythropoiesis in vivo, which in turn could be translated to the reduction of administration frequency to patients clinically.

While darbepoetin has been approved for clinical application with less-frequent injections to increase patient compliance and reduce the work burden on health care providers, these experimental data strongly indicate that rHuEPO-FcG disclosed herein has at least comparable potential benefits. As discussed above, darbepoetin, as a mutant analog of the human EPO molecule containing additional sugar compounds (increased glycosylation), may have an increased risk of inducing immunogenesis in vivo due to alteration of native three dimensional structures. Only long-term observation of patients undergoing treatment with darbepoetin will reveal the immunogenic risks of darbepoetin. In contrast, rHuEPO-FcG, which does not modify the EPO molecule portion, has a carbohydrate content identical or closely similar to that of native human EPO. The amount of sialic acids in the inventors' pure rHuEPO-FcG protein were approximately 10.0 mmol/mmol EPO, consistent with the reported parameters of rHuEPO. The Fc portion of rHuEPO-FcG, with no external amino acid(s)/linking peptide, represents the general structure of human IgG 1, and should not generate an immunogenic response. If approved clinically, rHuEPO-FcG may provide a better choice for patients than currently available rHuEPO and EPO analogs, especially those in need of long-term administration.

Figure 9:
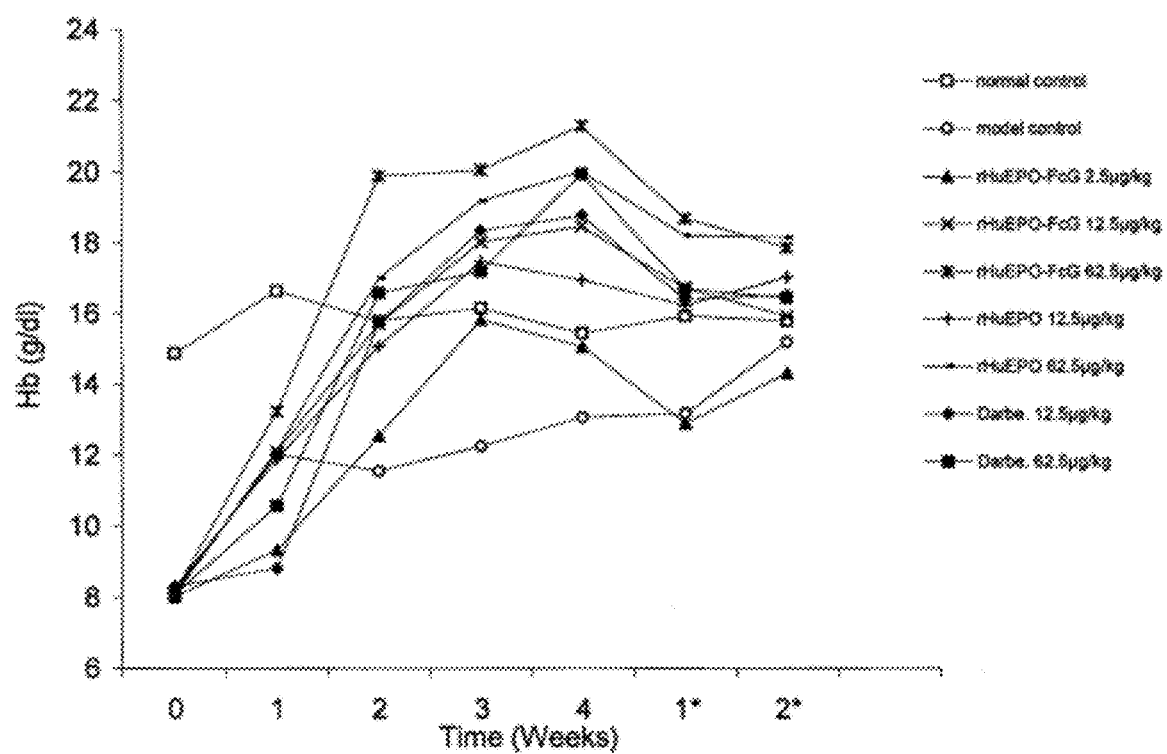
FIG. 9 is a graph showing the dose-dependent increase of hemoglobin (Hb) levels in 5/6 nephrectomized rats treated with once per week s.c. of rHuEPO-FcG, rHuEPO or darbepoetin-alfa (abbreviated Darbe.). Each point represents the mean Hb level of the group. Normal controls were normal rats with injection of carrier solution. Model controls were the 5/6 nephrectomized rats with injection of carrier solution. Week 0 levels represent the Hb levels before treatment. *: week(s) post treatment.

Intravenous injection once every two weeks, with each of rHuEPO-FcG and darbepoetin (62.5 µg/kg), induced identical increases of Hb levels in the rats with renal anaemia far above the normal Hb levels in the normal control rats (FIG. 9). This further demonstrates the persistent stimulation of erythropoiesis by rHuEPO-FcG.

Figure 10:
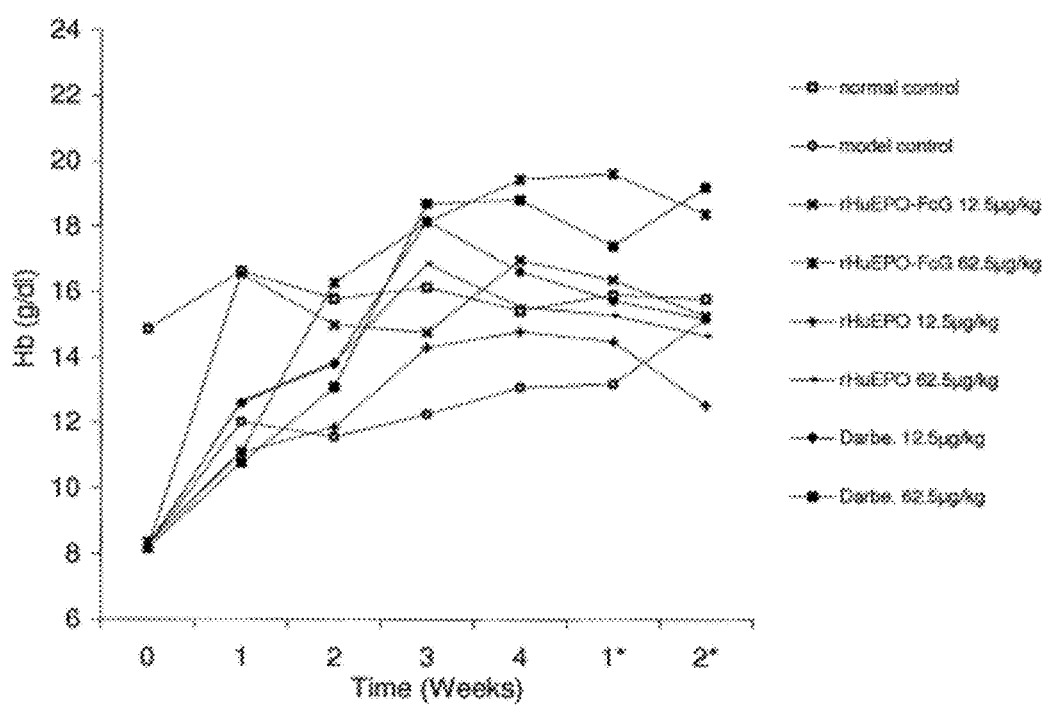
FIG. 10 is a graph showing the dose-dependent increase of hemoglobin (Hb) levels in 5/6 nephrectomized rats treated once every two weeks s.c. with rHuEPO-FcG, rHuEPO or darbepoetin-alfa (abbreviated Darbe.). Each point represents the mean Hb level of the group. Normal controls were normal rats with injection of carrier solution. Model controls were the 5/6 nephrectomized rats with injection of carrier solution. Week 0 levels represent the Hb levels before treatment. *: week(s) post treatment.
Figure 11:
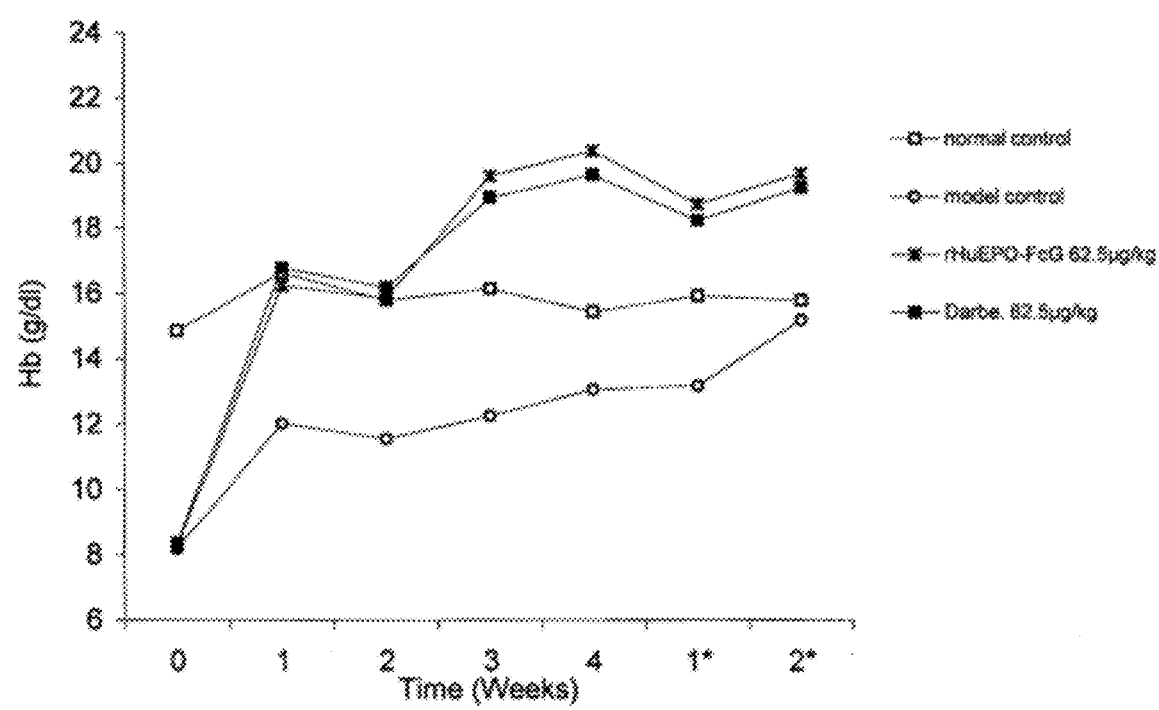
FIG. 11 is a graph showing the dose-dependent increase of hemoglobin (Hb) levels in 5/6 nephrectomized rats treated once every two weeks i.v. with 62.5 μg/kg of rHuEPO-FcG, or darbepoetin-alfa (abbreviated Darbe.). Each point represents the mean Hb level of the group. Normal controls were normal rats with injection of carrier solution. Model controls were the 5/6 nephrectomized rats with injection of carrier solution. Week 0 levels represent the Hb levels before treatment. *: week(s) post treatment.
Figure 12A:
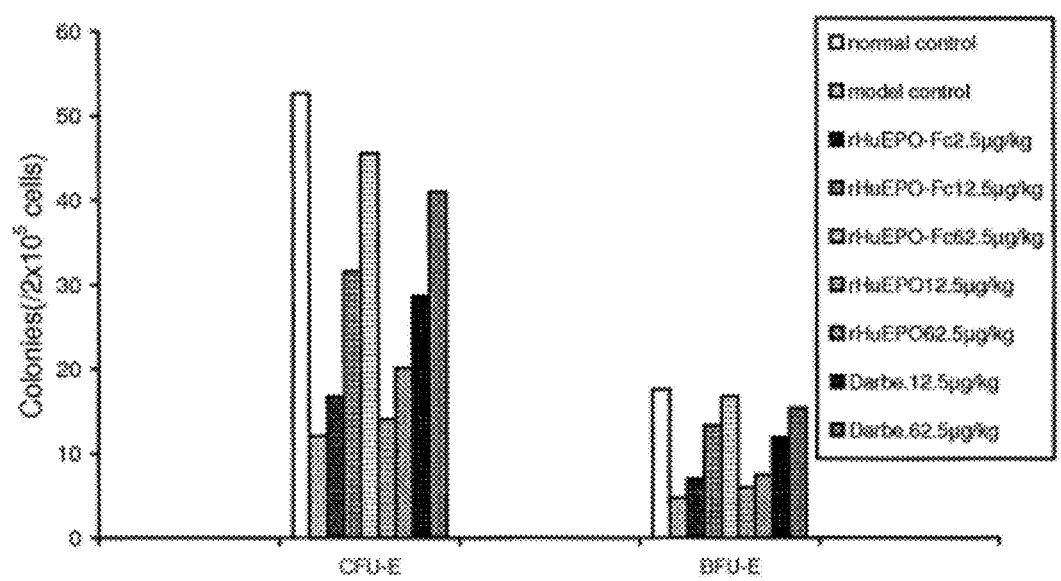
FIGS. 12A to 12C are graphs comparing the potency of rHuEPO-FcG, rHuEPO and darbepoetin-alfa in stimulating the colony formation of CFU-E and BFU-E in 5/6 nephrectomized rats treated with different doses and schedules. rHuEPO-FcG and darbepoietin-alpha (abbreviated Darbe.) treatment showed similar dose-dependent potencies for stimulating the CFU-E and BFU-E colony formation, while rHuEPO was less potent. A: s.c. once every week. B: s.c. once every 2 weeks. C: i.v. once every two weeks.
Figure 12B:
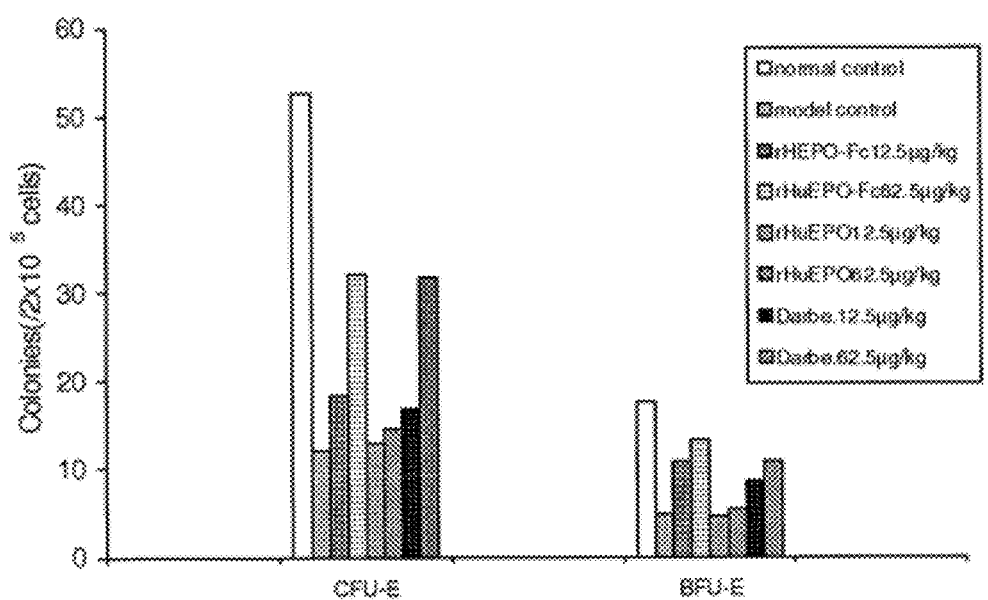
Figure 12C:
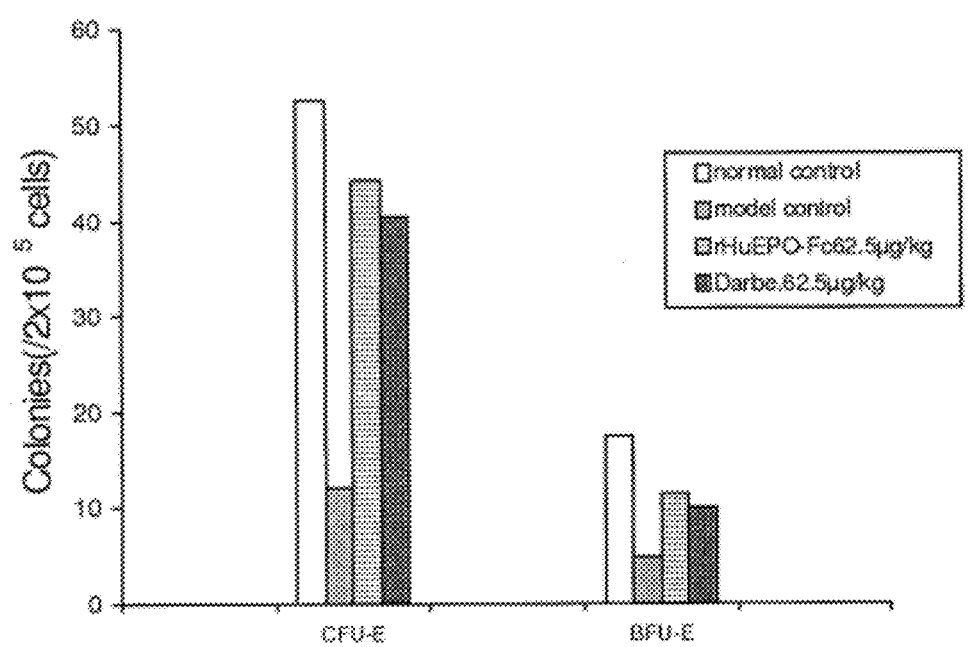

Data derived from cell culturing experiments of bone marrow cells collected from the 5/6 nephrectomized rats after treatments (once per week or per two weeks, s.c. or i.v.) showed that rHuEPO-FcG, rHuEPO and darbepoetin all stimulated the formation of CFU-E and BFU-E. The potencies of rHuEPO-FcG and darbepoetin were similar and stronger than that of rHuEPO (FIG. 10).

Blood urinonitrogen (BUN) and creatinine levels were similar in the treated groups and model control group. The levels of serum Fe in all the treated groups were higher than that of the model control group. Pathological examinations revealed increased distribution of red blood cell (RBC)-related cells in bone marrow and spleen of all EPO-treated rats.

8. Pharmacokinetic Studies of rHuEPO-FcG in Rhesus Monkeys

As discussed above, the inventors have designed rHuEPO-FcG in such a way that the EPO portion of the fusion protein retains the functional properties of natural EPO, such as stimulating erythropoiesis, and the Fc fragment of human IgG 1 allows the retention of the fusion protein in circulation, thus extending its half-life in vivo. The above animal studies have demonstrated the erythropoietic activities of rHuEPO-FcG are enhanced in comparison with rHuEPO. The inventors have also conducted pharmacokinetic studies to determine the in vivo half-life of rHuEPO-FcG in comparison to that of rHuEPO. Primates were used to generate data as they are biologically very similar to human beings.

Figure 13:
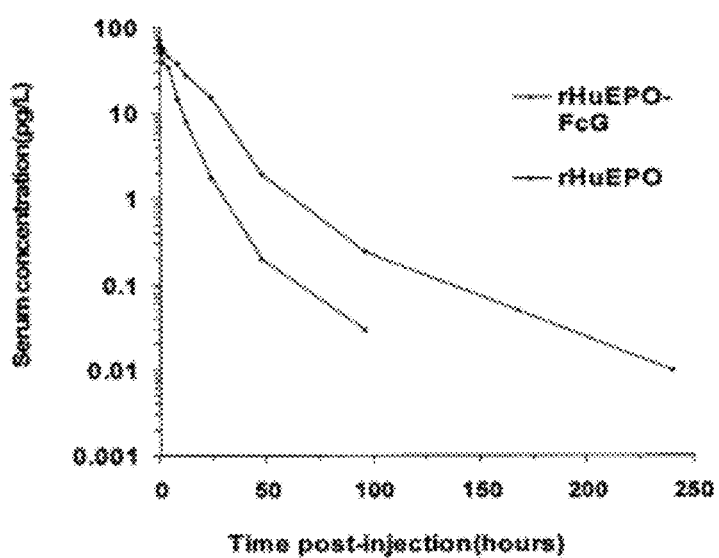
FIG. 13 is a graph showing the serum levels of rHuEPO-FcG and rHuEPO after the intravenous injection of 5 μg/kg of rHuEPO-FcG or rHuEPO to Rhesus monkeys (mean levels of 5 monkeys).

Study design was based on literature reports and the experiments were conducted according to the general guidelines of pharmacokinetics. Two groups of Rhesus monkeys with 5 monkeys in each group (3-5 kg, purchased from the Experiment Animal Center, AMMS, China) were injected intravenously with 5 µg/kg of rHuEPO-FcG or rHuEPO, respectively. Blood samples were taken before and at 0.017, 0.167, 0.5, 1, 2, 4, 8, 12, 24, 48, 96, 168 and 240 h after injection. Sera were collected by centrifugation and the serum rHuEPO-FcG or rHuEPO levels (summarized in FIG. 13) were determined by using human erythropoietin enzyme-linked immunosorbent assay (ELISA) kits (purchased from R&D Systems, Minneapolis, USA). The average half-life of rHuEPO-FcG and rHuEPO injected intravenously was 35.24+/−5.15 h and 8.72+/−1.69 h respectively.

To observe the bioavailability of rHuEPO-FcG, 5 µg/kg of rHuEPO-FcG was injected subcutaneously to 5 Rhesus monkeys. Blood samples were taken before and 1, 2, 5, 8, 10, 12, 15, 24, 48, 72, 96, 168 and 240 h after the injection, and the serum levels of rHuEPO-FcG were determined by the R&D kits. The bioavailability index was calculated as 35.71+/−5.37% with the subcutaneous injection. This is essentially identical to the reported bioavailability figures of darbepoetin-alpha (ARANESP) in patients with chronic renal failure.

This data demonstrates that rHuEPO-FcG has a significantly prolonged half-life in primates, and the in vivo half-life of rHuEPO-FcG is at least four fold longer than that of rHuEPO manufactured by Kirin Beer Brewing Co. of Japan. The prolonged half-life in vivo likely contributes to the enhanced erythropoietic activity of rHuEPO-FcG.

9. Immunogenicity of rHuEPO-FcG in *Macaca fascicularis*

As indicated above, the design of rHuEPO-FcG fusion protein intentionally avoids or minimizes changes of the immunogenic properties of the rHuEPO-FcG fusion protein. The inventors avoided including/adding any external amino acid(s) or linking peptide sequences in the fusion protein. According to one embodiment of the invention, the HuEPO-Fc fusion protein shown in FIG. 1B only contains the polypeptide sequences of the natural EPO protein and the Fc fragment (hinge region, CH2, CH3) of human IgG 1, and thus should not induce an immunogenic response nor the production of antibodies against rHuEPO-FcG protein.

Primate studies were conducted to observe the immunogenicity of rHuEPO-FcG protein. Ten crab-eating macaques (*Macaca fascicularis*) (male/female=5/5, ~5 years old, average weight of male 4.0±0.3 kg, female is 2.9±0.4 kg, purchased from Laboratory Animal Center, AMMS, China) were injected subcutaneously with 5 µg/kg of purified rHuEPO-FcG three times per week for four weeks, and two were injected with an equal volume of carrier solution as the control animals. Sera were collected once a week for 5 weeks (1 week post-treatment) and tested for the specific antibodies against rHuEPO-FcG by ELISA using purified rHuEPO-FcG (5 µg/ml) as the coating antigen. In addition, RBC counts and Hb levels in the peripheral blood were also determined within the experimental period. The resulting data shows that, while enhancement of erythropoiesis in the rHuEPO-FcG-treated macaques was observed (the mean RBC numbers increased from $4.74 \times 10^9$/ml to $6.67 \times 10^9$/ml and the mean Hb levels increased from 12.2 g/dl to 13.7 g/dl), rHuEPO-FcG did not induce the production of any detectable specific antibodies against the fusion protein. These results indicate that rHuEPO-FcG fusion protein does not cause immunogenicity in primates.

10. Acute Toxicity Studies of rHuEPO-FcG in Normal Mice

To assess the safety of rHuEPO-FcG fusion protein, acute toxic studies were conducted in animals.

Two groups of BALB/c mice (n=20, equal numbers of male and female, 5-6 weeks old, the average weight of female is 15.8±0.4 g, male is 15.9±0.6 g, purchased from Chinese Academy of Medicine, China) were injected intravenously once with an excessive amount of purified rHuEPO-FcG (male=13.3 mg/kg, female=13.2 mg/kg) or equal volume of the carrier solution via their tail veins. In addition to observing the instant reaction following injection, general behaviour and status, activities, eating and defecation patterns and changes were monitored and recorded daily for 14 days. All mice were also weighed at day 7 and day 14. At day 15 post-injection, anatomical examination of the main organs of the mice were conducted. Pathologic examination were to be conducted if any unusual changes or suspicious changes of the organs were observed.

All mice in the 2 groups had no obvious instant reaction following injection. Within the period of 14 days, no obvious changes of behaviour, activities, eating and defecation patterns were observed. Moreover, the weight of the mice in both groups increased steadily during the testing period, and no apparent differences were found between the 2 groups on day 7 or day 14 post injection. No abnormal or pathologic changes were detected in the tissues of brain, lung, heart, liver and kidney. These results indicate that administration of an excessive amount of rHuEPO-FcG, far more than required for exhibiting the normal erythropoiesis function, is safe and had no apparent toxic effects.

11. Comparison of Wild Type and Mutated Fusion Proteins of rHuEPO-FcC and rHuEPO-FcG Investigations were also conducted to compare wild type and mutated versions of proteins of HuEPO-Fc. As described above, in one embodiment the invention includes a single amino acid mutation at amino acid residue 172 (C172G).

In vivo experiments in mice were conducted to compare the erythropoietic activity of the wild type fusion protein rHuEPO-FcC with the mutated fusion protein rHuEPO-FcG Q-and with recombinant human EPO (rHuEPO). For comparison purpose, all the doses of the three proteins used in this example, namely rHuEPO-FcG, rHuEPO-FcC and rHuEPO, were the amounts of the EPO molecule portion alone on a molar basis. In respect of the rHuEPO-FcG and rHuEPO-FcC proteins, the EPO portion contributes 41.4% of the total rHuEPO-FcG molecular weight as calculated by the ratio of the weight of amino acids of EPO to the weight of the total amino acids of the whole rHuEPO-FcG and rHuEPO-FcC molecules (i.e., 166 of 399 amino acids).

rHuEPO-FcG (stock concentration: 300 µg/ml), rHuEPO-FcC (stock concentration: 90 µg/ml) and rHuEPO with the natural human EPO structure (6000 IU/0.5 ml, manufactured by Kirin Brewery Co., Japan) were diluted in carrier solution (2.5 mg/ml of human serum albumin, 5.8 mg/ml of sodium citrate, 0.06 mg/ml of citric acid and 5.8 mg/ml of sodium chloride, pH 5.5-5.6). The dose of rHuEPO was calculated according to its activity/amount ratio. BALB/c mice (9 to 10 weeks old, weighing 18-22 g, equal numbers of male and female, purchased from Experiment Animal Center, AMMS, China) were grouped randomly with 8 in each group. Each group of mice was treated with one combination of one dose (2.5, 12.5, 62.5 µg/kg), one injection route (s.c.) and one injection schedule (three times per week or once per week). The control group of mice was injected with an equal volume of carrier solution. Treatment lasted for 26 days. Peripheral blood samples (tail vein) for measurement were taken before treatment on the $2^{nd}$, $6^{th}$, $9^{th}$, $16^{th}$, $19^{th}$, $22^{nd}$ and $26^{th}$ days of treatment. Hb was measured as the index by absorptiometry. Mean±SD was calculated from the data of each group and a t test was conducted among different groups.

Figure 14:
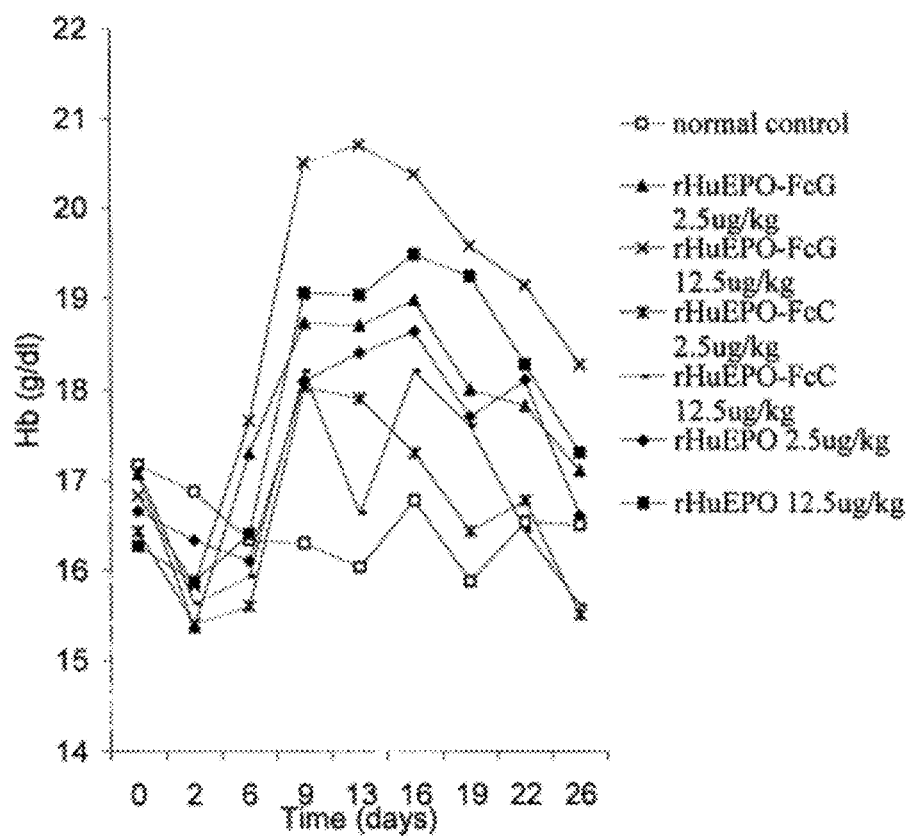
FIG. 14 is a graph showing the dose-dependent increase of hemoglobin (Hb) levels in normal mice treated three times per week with subcutaneous injection (s.c.) of rHuEPO-FcG, rHuEPO-FcC and rHuEPO. Each point represents the mean Hb level of the group (8). Normal control was normal mice with injection of carrier solution. Day 0 levels represent the Hb levels before treatment.

The administration of EPO three times per week to mice induced saturated stimulation of erythropoiesis. As shown in FIG. 14, the mice treated by rHuEPO-FcG 3 times per week s.c. had significant elevation of Hb levels even at the dose of 2.5 ug/kg at the $9^{th}$ day after treatment. The elevation of Hb levels in the treated group was dose-dependent. However, saturated elevation of the Hb levels was induced in mice at the dose of 12.5 ug/kg of rHuEPO-FcG. The elevation of Hb levels induced by 2.5 ug/kg of rHuEPO-FcG was also greater than that by 2.5 ug/kg of rHuEPO-FcC and rHuEPO. These results suggested more potent erythropoietic stimulation by rHuEPO-FcG.

Figure 15:
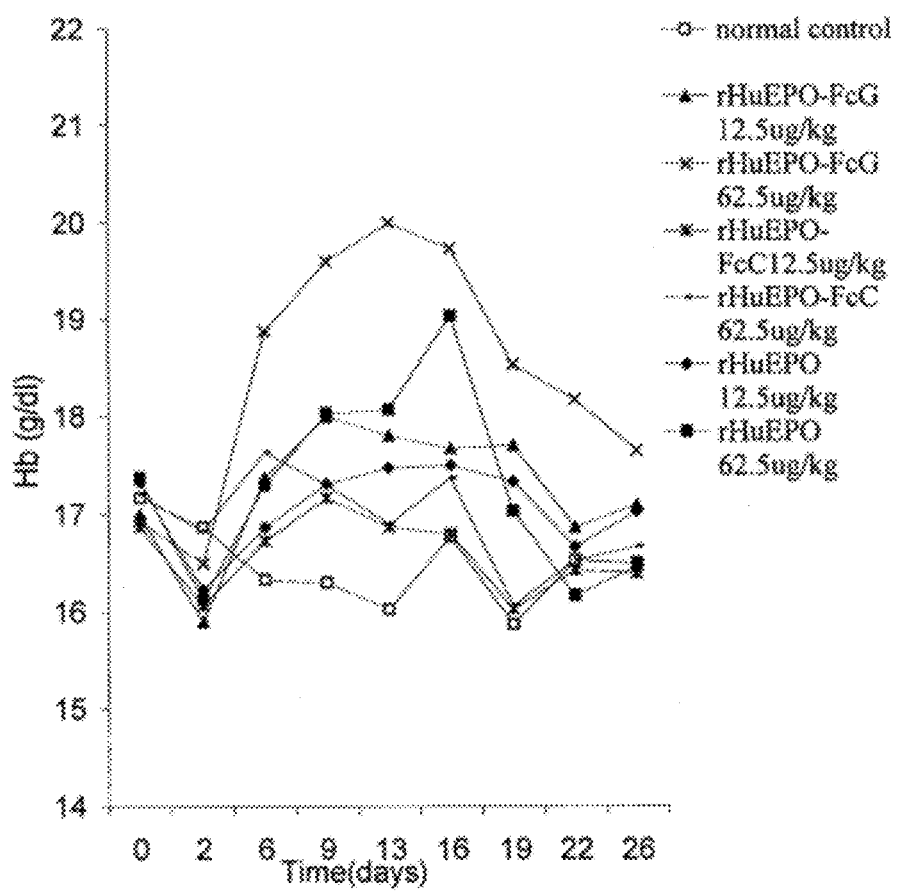
FIG. 15 is a graph showing the dose-dependent increase of hemoglobin (Hb) levels in normal mice treated once per week with subcutaneous injection (s.c.) of rHuEPO-FcG, rHuEPO-FcC and rHuEPO. Each point represents the mean Hb level of the group (8). Normal control was normal mice with injection of carrier solution. Day 0 levels represent the Hb levels before treatment.

The erythropoietic potency of rHuEPO-FcG was further explored by reducing the injection times to once per week subcutaneously. As shown in FIG. 15, the rHuEPO-FcG treated groups showed dose-dependent elevation of Hb levels at the doses of 12.5, or 62.5 ug/kg. Both doses of 12.5 and 62.5 ug/kg of rHuEPO also induced the elevation of Hb levels to the similar extent, which was much lower than that by 62.5 ug/kg of rHuEPO-FcG. The rHuEPO-FcC-treated groups showed significantly lower Hb levels. This strongly indicates that rHuEPO-FcG has enhanced erythropoietic activity in vivo. It is presumably due to either improved EPO receptor binding/activation by the dimer EPO molecules in rHuEPO-FcG protein or by the possible prolonged half-life of rHuEPO-FcG in vivo, or due to the combined effects of both.

The results demonstrated that rHuEPO-FcG exhibited an enhanced in vivo erythropoietic activity compared to rHuEPO-FcC and rHuEPO. This enhanced activity appears to be attributable to the single amino acid mutation in the hinge region of the recombinant molecule at residue 172 (Fig. 2B). The results show that rHuEPO-FcC exhibited very little erythropoietic activity in normal mice and much less erythropoietic activity compared to rHuEPO-FcG and rHuEPO.

12. Enhanced Therapeutic Effects of rHuGMCSF-FcG for Neutropenia in $^{60}$Co-Irradiated Dogs The enhanced biological activity of rHuGMCSF-FcG was observed in model dogs with neutropenia induced by $^{60}$Co γ-ray irradiation. The efficacy of rHuGMCSF-FcG was also compared with that of native GM-CSF.

rHuGMCSF-FcG (stock concentration: 1.8 mg/ml, purity 98%) and native human rHuGM-CSF (150 µg/vial, manufactured by NCPC GeneTech Biotechnology Development Co., Ltd., China) were diluted in carrier solution (1% of HSA, 1.1% of benzyl alcohol, 40 mg/ml of mannitol, 10 mg/ml of sucrose, and 1.2 mg/ml of tromethamine).

Beagle dogs (male and female in equal number, weighing 8-10 kg, 12-15 months old, purchased from Beijing Xieerxin Institute of BioResources. Licence No. SOCK 2005-0005, China) were divided into 4 groups (4 in each group) randomly: model control, low dose of rHuGMCSF-FcG (10 µg/kg), high dose of rHuGMCSF-FcG (20 µg/kg), and high dose of rHuGMCSF (20 µg/kg). Each dog, with the pelvis shielded by lead blocks, was irradiated by 6.5 Gy of $^{60}$Co γ-ray at a rate of 295.54 rad/min. The treatment started from the next day of irradiation by subcutaneous injection, once every other day for rHuGMCSF-FcG, or once every day for rHuGMCSF. The dogs from control group were injected with an equal volume of carrier solution. Injections were given over 10 days and the total observation time was 28 days. After irradiation, the dogs were examined each day for their general clinical conditions. Every other day, peripheral blood was collected for examinations of WBC count, platelet count, RBC count, HB, and hematocrit (Hct).

Figure 16:
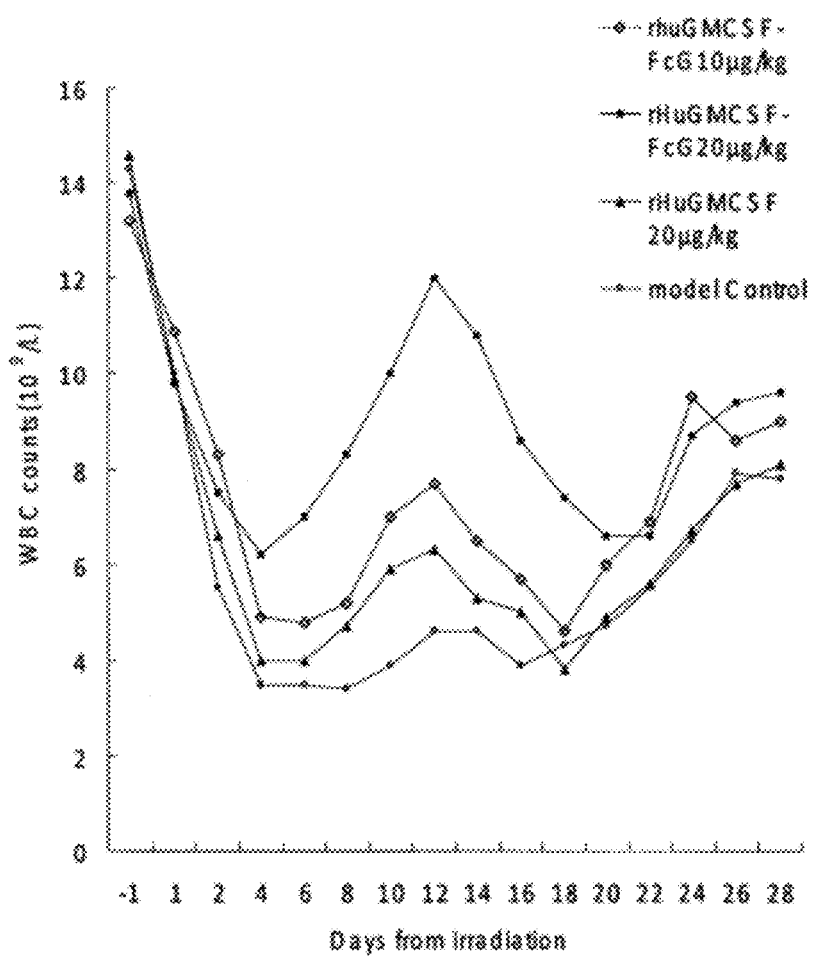
FIG. 16 is a graph comparing the growth of white blood cells (WBC) in dogs with experimental neutropenia by rHuGMCSF-FcG or by rHuGMCSF. $^{60}$Co γ-ray irradiated dogs were treated s.c. with 10 μg/kg of rHuGMCSF-FcG every other day, 20 μg/kg of rHuGMCSF-FcG every other day, or 20 μg/kg of rHuGMCSF every day. Day −1 and day 1 represent the day before irradiation and the next day after irradiation respectively. Treatment started from day 1 and lasted for 10 days. Clinical observation and examination of WBC counts lasted for 28 days. Each point represents the mean WBC counts of the group. Model controls were the irradiated dogs with injection of carrier solution only.

As shown in FIG. 16, all the irradiated dogs developed neutropenia immediately after irradiation. Since dogs from control group were only injected with carrier solution, their clinical courses reflected natural recovery with no treatment. WBC counts decreased dramatically the day following irradiation and reached a nadir by day 4. The low WBC count lasted for another 4-5 days. After that, it began increasing slowly, indicating the recovery from neutropenia.

Dogs from the three administrated groups also developed similar neutropenia after irradiation, but their WBC counts showed rapid and sustained increases during the course of treatment. All the nadirs of WBC counts were raised compared with control group. Furthermore, the duration of low WBC counts was also shorter. The increasing of WBC reached its peak on the day following the last injection. These results indicate that both rHuGMCSF-FcG and rHuGMCSF induced hematopoietic recovery.

Different levels of activity were observed within the three administrated groups. rHuGMCSF-FcG demonstrated enhanced hematopoietic recovery compared with rHuGMCSF. Despite only being administrated every other day, the dogs injected with rHuGMCSF-FcG showed stronger recovery potency than dogs with rHuGMCSF administrated daily. While the dogs injected with low doses of rHuGMCSF-FcG (10 µg/kg) and high doses of rHuGMCSF (20 µg/kg) showed similar WBC counts and recovery tendency, the WBC counts from dogs with high doses of rHuGMCSF-FcG (20 µg/kg) were twice as high as the other two groups during the entire course of recovery. This dose-dependent, persistent elevation further indicates that rHuGMCSF-FcG possesses enhanced biological activity compared to its native counterpart (FIG. 16).

The enhanced biological activity of rHuGMCSF-FcG in vivo, similar to that discussed in rHuEPO-FcG experiments, is also presumably due to improved GM-CSF receptor binding/activation by the dimer GM-CSF molecules in rHuGMCSF-FcG protein, the possible prolonged half-life of rHuGMCSF-FcG in vivo, or due to the combined effects of both.

As will be apparent to those skilled in the art in the light of the foregoing disclosure, many alterations and modifications are possible in the practice of this invention without departing from the spirit or scope thereof.

REFERENCES

1. Capon, et al., Designing CD4 immunoadhesins for AIDS therapy, Nature 337:525-531, 1989.
2. Yeh et al., Design of yeast-secreted albumin derivatives for human therapy: Biological and antiviral properties of a serum albumin-CD4 genetic conjugate, PNAS 89:1904-1908, 1992.
3. Jones, et al., The development of a modified human IFN-α2b linked to the Fc portion of human IgG1 as a novel potential therapeutic for the treatment of hepatitis C virus infection, Journal of Interferon and Cytokine Research 24:560-572, 2004.
4. Lo et al., High level expression and secretion of Fc-X fusion proteins in mammalian cells, Protein engineering 11(6), 495-500, 1998.
5. U.S. Pat. No. 5,723,125 Chang et al., Hybrid with interferon-alpha and an immunoglobulin Fc linked through a non-immunogenic peptide.
6. U.S. Pat. No. 5,908,626, Chang et al., Hybrid with interferon-beta. and an immunoglobulin Fc joined by a peptide linker.
7. U.S. Pat. No. 5,914,111, Wallner et al., CD2-binding domain of lymphocyte function associated antigen-3.
8. U.S. Pat. No. 6,165,476, Strom et al., Fusion proteins with an immunoglobulin hinge region linker.
9. U.S. Pat. No. 6,403,077, Strom et al., Treatment regimes featuring an IL-10-containing chimeric polypeptide.
10. U.S. Pat. No. 6,797,493, Sun et al., Fc fusion proteins of human granulocyte colony-stimulating factor with increased biological activities.
11. U.S. Pat. No. 6,808,902, Treuheit et al., Process for correction of a disulfide misfold in IL-1ra FC fusion molecules
12. U.S. Pat. No. 6,900,292, Sun et al., Fc fusion proteins of human erythropoietin with increased biological activities.
13. U.S. Pat. No. 7,030,226, Sun et al., Fc fusion proteins of human erythropoietin with increased biological activities.
14. U.S. Pat. No. 7,067,110, Gillies et al., Fc fusion proteins for enhancing the immunogenicity of protein and peptide antigens.
15. U.S. Pat. No. 7,091,321, Gilles et al., Enhancing the circulating half-life of antibody-based fusion proteins.
16. U.S. Pat. No. 7,112,659, Mann et al., OB fusion protein compositions and methods.
17. U.S. Pat. No. 7,189,827, Feige, Modified peptides as therapeutic agents.
18. U.S. Pat. No. 7,211,253, Way, Erythropoietin forms with improved properties.
19. U.S. Pat. No. 7,217,798, Hinton et al., Alteration of Fc-fusion protein serum half-lives by mutagenesis.
20. U.S. Pat. No. 7,226,759, Sun et al., Fc fusion proteins of human granulocyte colony-stimulating factor with increased biological activities.
21. U.S. Pat. No. 7,232,668, Sun et al., Fc fusion proteins of human granulocyte colony-stimulating factor with increased biological activities.
22. United States Patent Application No. 20010053539. Lauffer et al., Fusion proteins with immunoglobulin proteins, the preparation and use thereof.
23. United States Patent Application No. 20020081664, Lo et al., Expression and export of interferon-alpha proteins as Fc fusion proteins.
24. United States Patent Application No. 20030105294, Gillies et al., Enhancing the circulating half life of antibody-based fusion proteins.

25. United States Patent Application No. 20030166877, Gillies et al., Reducing the immunogenicity of fusion proteins.
26. United States Patent Application No. 20050069521, Gillies et al., Enhancing the circulating half-life of interleukin-2 proteins.
27. Mohler, et al., Soluble tumor necrosis factor (TNF) receptors are effective therapeutic agents in lethal endotoxemia and function simultaneously as both TNF carriers and TNF antagonists, The Journal of Immunology 151 (3):1548-1561, 1993.
28. Goldenberg, Etanercept, a novel drug for the treatment of patients with severe, active rheumatoid arthritis, Clin. Ther. 21(1):75-87, 1999.
29. Wong et al., The use of alefacept in the treatment of psoriasis. Skin Therapy Letter 8(6):1-2(2003)
30. Way et al., Improvement of Fc-erythropoietin structure and pharmacokinetics by modification at a disulfide bond, Protein Engineering, Design & Selection 18(3):111-118, 2005.

What is claimed is:

1. A fusion protein comprising from N-terminus to C-terminus:
    a non-immunoglobulin polypeptide comprising a cysteine residue nearest to the C-terminus, wherein said polypeptide is selected from the group consisting of human erythropoietin (EPO) and human granulocyte-macrophage colony stimulating factor (GM-CSF); and
    an immunoglobulin component comprising a human IgG1 Fc fragment having a mutated IgG1 hinge region, wherein the non-immunoglobulin polypeptide is directly coupled to the immunoglobulin component without an external linker peptide,
    wherein said IgG1 Fc fragment comprises said IgG1 mutated hinge region and IgG1 CH2 and CH3 domains;
    wherein the amino acid sequence of said mutated IgG1 hinge region is set forth in VEPKSGDKTSTCPPCP (SEQ ID NO: 24) or the amino acid sequence of SEQ ID NO:24, wherein one or more amino acid residues N-terminal to the glycine residue is deleted in SEQ ID NO:24; and
    wherein the fusion protein has enhanced biological activity in vivo in comparison to the native non-immunoglobulin polypeptide and in comparison to a fusion protein comprising the native non-immunoglobulin polypeptide and a human IgG1 Fc fragment comprising a native IgG1 hinge region and IgG1 CH2 and CH3 domains.

2. A fusion protein according to claim 1, wherein the non-immunoglobulin polypeptide is human granulocyte-macrophage colony stimulating factor.

3. A multimeric protein comprising a plurality of fusion proteins according to claim 1.

4. The multimeric protein according to claim 3 wherein the multimeric protein is a dimer.

5. A pharmaceutical composition comprising a fusion protein according to claim 2 and a pharmaceutically acceptable carrier, adjuvant or diluent.

6. A fusion protein comprising from N-terminus to C-terminus:
    a non-immunoglobulin polypeptide selected from the group consisting of human erythropoietin (EPO) and human granulocyte-macrophage colony stimulating factor (GM-CSF); and
    an immunoglobulin component comprising a human IgG1 Fc fragment having a mutated IgG1 hinge region wherein the non-immunoglobulin polypeptide is directly coupled to the immunoglobulin component without an external linker peptide, wherein said IgG1 Fc fragment comprises said mutated IgG1 hinge region and IgG1 CH2 and CH3 domains,
    wherein the amino acid sequence of said mutated IgG1 hinge region is set forth in VEPKSGDKTSTCPPCP (SEQ ID NO: 24) or the amino acid sequence of SEQ ID NO:24, wherein one or more amino acid residues N-terminal to the glycine residue is deleted in SEQ ID NO:24; and
    wherein the fusion protein has enhanced biological activity in vivo in comparison to the native non-immunoglobulin polypeptide and in comparison to a fusion protein comprising the native non-immunoglobulin polypeptide and a human IgG1 Fc fragment comprising a native IgG1 hinge region and IgG1 CH2 and CH3 domains.

7. A fusion protein comprising from N-terminus to C-terminus: (i) a non-immunoglobulin polypeptide selected from the group consisting of human erythropoietin (EPO) and human granulocyte-macrophage colony stimulating factor (GM-CSF) and (ii) a human immunoglobulin component comprising an IgG1 Fc fragment, wherein the fusion protein has a prolonged half-life in vivo in comparison to naturally occurring or recombinant native non-immunoglobulin polypeptide, and wherein the non-immunoglobulin polypeptide is directly coupled to the immunoglobulin component without an external linker peptide, wherein said IgG1 Fc fragment comprises a mutated IgG1 hinge region and IgG1 CH2 and CH3 domains, wherein the amino acid sequence of said mutated IgG1 hinge region is set forth in VEPKSGDKTSTCPPCP (SEQ ID NO: 24) or the amino acid sequence of SEQ ID NO:24, wherein one or more amino acid residues N-terminal to the glycine residue is deleted in SEQ ID NO:24; and wherein the fusion protein has enhanced biological activity in vivo in comparison to the native non-immunoglobulin polypeptide and in comparison to a fusion protein comprising the native non-immunoglobulin polypeptide and a human IgG1 Fc fragment comprising a native IgG1 hinge region and IgG1 CH2 and CH3 domains.

8. The fusion protein according to claim 7, wherein the half-life of the fusion protein is at least three fold higher than the native non-immunoglobulin polypeptide.

9. The fusion protein according to claim 7, wherein the half-life of the fusion protein is at least four fold higher than the native non-immunoglobulin polypeptide.

10. A fusion protein according to claim 7, wherein the non-immunoglobulin polypeptide is a-human granulocyte-macrophage colony stimulating factor.

11. A multimeric protein comprising a plurality of fusion proteins according to claim 7.

12. The multimeric protein according to claim 11 wherein the multimeric protein is a dimer.

13. A pharmaceutical composition comprising a fusion protein according to claim 10 and a pharmaceutically acceptable carrier, adjuvant or diluent.

14. A fusion protein comprising the amino acid sequence of SEQ ID NO:6.

15. The fusion protein as defined in claim 1, wherein the amino acid sequence of said mutated IgG1 hinge region is set forth in VEPKSGDKTSTCPPCP (SEQ ID NO:24).

16. The fusion protein as defined in claim 1, wherein one amino acid N-terminal to the glycine residue is deleted in SEQ ID NO:24.

17. A fusion protein comprising from N-terminus to C-terminus a non-immunoglobulin polypeptide selected from the group consisting of human EPO and human GM-CSF, a mutated human IgG1 hinge region, wherein the amino acid sequence of the mutated human IgG1 hinge region is set forth in SEQ ID NO:24, and human IgG1 CH2 and CH3 domains.

18. The fusion protein as defined in claim 6, wherein the amino acid sequence of said mutated IgG1 hinge region is set forth in VEPKSGDKTSTCPPCP (SEQ ID NO:24).

19. The fusion protein as defined in claim 6, wherein one amino acid N-terminal to the glycine residue is deleted in SEQ ID NO:24.

20. The fusion protein as defined in claim 7, wherein the amino acid sequence of said mutated IgG1 hinge region is set forth in VEPKSGDKTSTCPPCP (SEQ ID NO:24).

21. The fusion protein as defined in claim 7, wherein one amino acid N-terminal to the glycine residue is deleted in SEQ ID NO:24.

22. A multimeric protein comprising a plurality of fusion proteins according to claim 6.

23. The multimeric protein according to claim 22 wherein the multimeric protein is a dimer.

24. A multimeric protein comprising a plurality of fusion proteins according to claim 17.

25. The multimeric protein according to claim 24 wherein the multimeric protein is a dimer.

* * * * *

SEQUENCE LISTING

```
<160> NUMBER OF SEQ ID NOS: 24

<210> SEQ ID NO 1
<211> LENGTH: 1281
<212> TYPE: DNA
<213> ORGANISM: Artificial
<220> FEATURE:
<223> OTHER INFORMATION: DNA encoding rHuEPO-FcG fusion protein

<400> SEQUENCE: 1 atggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttctatgc ctggaagagg     240
atggaggtcg ggcagcaggc cgtagaagtc tggcagggcc tggccctgct gtcggaagct     300
gtcctgcggg gccaggccct gttggtcaac tcttcccagc cgtgggagcc cctgcagctg     360
catgtggata aagccgtcag tggccttcgc agcctcacca ctctgcttcg ggctctgcga     420
gcccagaagg aagccatctc ccctccagat gcggcctcag ctgctccact ccgaacaatc     480
actgctgaca ctttccgcaa actcttccga gtctactcca atttcctccg gggaaagctg     540
aagctgtaca caggggaggc ctgcaggaca ggggacagag ttgagcccaa atctggtgac     600
aaaactagta catgcccacc gtgcccagca cctgaactcc tggggggacc gtcagtcttc     660
ctcttccccc caaaacccaa ggacaccctc atgatctccc ggacccctga ggtcacatgc     720
gtggtggtgg acgtgagcca cgaagaccct gaggtcaagt tcaactggta cgtggacggc     780
gtggaggtgc ataatgccaa gacaaagccg cgggaggagc agtacaacag cacgtaccgt     840
gtggtcagcg tcctcaccgt cctgcaccag gactggctga atggcaagga gtacaagtgc     900
aaggtctcca acaaagccct cccagccccc atcgagaaaa ccatctccaa agccaaaggg     960
cagccccgag aaccacaggt gtacaccctg cccccatccc gggatgagct gaccaagaac    1020
caggtcagcc tgacctgcct ggtcaaaggc ttctatccca gcgacatcgc cgtggagtgg    1080
gagagcaatg ggcagccgga gaacaactac aagaccacgc tcccgtgct ggactccgac     1140 ggcccttct tcctctacag caagctcacc gtggacaaga gcaggtggca gcaggggaac    1200
gtcttctcat gctccgtgat gcatgaggct ctgcacaacc actacacgca gaagagcctc    1260
tccctgtctc cgggtaaata a                                              1281

<210> SEQ ID NO 2
<211> LENGTH: 426
<212> TYPE: PRT
<213> ORGANISM: Artificial
<220> FEATURE:
<223> OTHER INFORMATION: amino acid sequence of rHuEPO-FcG fusion
      protein
```

<400> SEQUENCE: 2

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Arg Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Val Glu Pro Lys Ser Gly Asp Lys Thr Ser Thr Cys Pro Pro Cys
        195                 200                 205

Pro Ala Pro Glu Leu Leu Gly Gly Pro Ser Val Phe Leu Phe Pro Pro
    210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
                245                 250                 255

Tyr Val Asp Gly Val Glu Val His Asn Ala Lys Thr Lys Pro Arg Glu
            260                 265                 270

Glu Gln Tyr Asn Ser Thr Tyr Arg Val Val Ser Val Leu Thr Val Leu
        275                 280                 285

His Gln Asp Trp Leu Asn Gly Lys Glu Tyr Lys Cys Lys Val Ser Asn
    290                 295                 300

Lys Ala Leu Pro Ala Pro Ile Glu Lys Thr Ile Ser Lys Ala Lys Gly
305                 310                 315                 320

Gln Pro Arg Glu Pro Gln Val Tyr Thr Leu Pro Pro Ser Arg Asp Glu
                325                 330                 335

Leu Thr Lys Asn Gln Val Ser Leu Thr Cys Leu Val Lys Gly Phe Tyr
            340                 345                 350

Pro Ser Asp Ile Ala Val Glu Trp Glu Ser Asn Gly Gln Pro Glu Asn
        355                 360                 365

Asn Tyr Lys Thr Thr Pro Pro Val Leu Asp Ser Asp Gly Pro Phe Phe
    370                 375                 380

Leu Tyr Ser Lys Leu Thr Val Asp Lys Ser Arg Trp Gln Gln Gly Asn
385                 390                 395                 400

Val Phe Ser Cys Ser Val Met His Glu Ala Leu His Asn His Tyr Thr
                405                 410                 415
```

Gln Lys Ser Leu Ser Leu Ser Pro Gly Lys
            420                 425

<210> SEQ ID NO 3
<211> LENGTH: 1281
<212> TYPE: DNA
<213> ORGANISM: Artificial
<220> FEATURE:
<223> OTHER INFORMATION: DNA encoding rHuEPO-FcC fusion protein

<400> SEQUENCE: 3

```
atggggtgc acgaatgtcc tgcctggctg tggcttctcc tgtccctgct gtcgctccct      60
ctgggcctcc cagtcctggg cgccccacca cgcctcatct gtgacagccg agtcctggag    120
aggtacctct tggaggccaa ggaggccgag aatatcacga cgggctgtgc tgaacactgc    180
agcttgaatg agaatatcac tgtcccagac accaaagtta atttctatgc ctggaagagg    240
atggaggtcg ggcagcaggc cgtagaagtc tggcagggcc tggccctgct gtcggaagct    300
gtcctgcggg gccaggccct gttggtcaac tcttcccagc cgtgggagcc cctgcagctg    360
catgtggata aagccgtcag tggccttcgc agcctcacca ctctgcttcg ggctctgcga    420
gcccagaagg aagccatctc ccctccagat gcggcctcag ctgctccact ccgaacaatc    480
actgctgaca ctttccgcaa actcttccga gtctactcca atttcctccg gggaaagctg    540
aagctgtaca aggggaggc ctgcaggaca ggggacagag ttgagcccaa atcttgtgac    600
aaaactagta catgcccacc gtgcccagca cctgaactcc tggggggacc gtcagtcttc    660
ctcttccccc caaaacccaa ggacaccctc atgatctccc ggaccctga ggtcacatgc    720
gtggtggtgg acgtgagcca cgaagaccct gaggtcaagt tcaactggta cgtggacggc    780
gtggaggtgc ataatgccaa gacaaagccg cgggaggagc agtacaacag cacgtaccgt    840
gtggtcagcg tcctcaccgt cctgcaccag gactggctga atggcaagga gtacaagtgc    900
aaggtctccaa caaagccct cccagccccc atcgagaaaa ccatctccaa agccaaaggg    960
cagccccgag aaccacaggt gtacaccctg cccccatccc gggatgagct gaccaagaac   1020
caggtcagcc tgacctgcct ggtcaaaggc ttctatccca gcgacatcgc cgtggagtgg   1080
gagagcaatg ggcagccgga gaacaactac aagaccacgc ctcccgtgct ggactccgac   1140
ggccccttct tcctctacag caagctcacc gtggacaaga gcaggtggca gcaggggaac   1200
gtcttctcat gctccgtgat gcatgaggct ctgcacaacc actacacgca gaagagcctc   1260
tccctgtctc cgggtaaata a                                              1281
```

<210> SEQ ID NO 4
<211> LENGTH: 426
<212> TYPE: PRT
<213> ORGANISM: Artificial
<220> FEATURE:
<223> OTHER INFORMATION: amino acid sequence of rHuEPO-FcC fusion
      protein

<400> SEQUENCE: 4

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu

```
            50                  55                  60
Asn Ile Thr Val Pro Asp Thr Lys Val Asn Phe Tyr Ala Trp Lys Arg
 65                  70                  75                  80
Met Glu Val Gly Gln Gln Ala Val Glu Val Trp Gln Gly Leu Ala Leu
                 85                  90                  95
Leu Ser Glu Ala Val Leu Arg Gly Gln Ala Leu Leu Val Asn Ser Ser
            100                 105                 110
Gln Pro Trp Glu Pro Leu Gln Leu His Val Asp Lys Ala Val Ser Gly
        115                 120                 125
Leu Arg Ser Leu Thr Thr Leu Leu Arg Ala Leu Arg Ala Gln Lys Glu
    130                 135                 140
Ala Ile Ser Pro Pro Asp Ala Ala Ser Ala Ala Pro Leu Arg Thr Ile
145                 150                 155                 160
Thr Ala Asp Thr Phe Arg Lys Leu Phe Arg Val Tyr Ser Asn Phe Leu
                165                 170                 175
Arg Gly Lys Leu Lys Leu Tyr Thr Gly Glu Ala Cys Arg Thr Gly Asp
            180                 185                 190
Arg Val Glu Pro Lys Ser Cys Asp Lys Thr Ser Thr Cys Pro Pro Cys
        195                 200                 205
Pro Ala Pro Glu Leu Leu Gly Gly Pro Ser Val Phe Leu Phe Pro Pro
    210                 215                 220
Lys Pro Lys Asp Thr Leu Met Ile Ser Arg Thr Pro Glu Val Thr Cys
225                 230                 235                 240
Val Val Val Asp Val Ser His Glu Asp Pro Glu Val Lys Phe Asn Trp
                245                 250                 255
Tyr Val Asp Gly Val Glu Val His Asn Ala Lys Thr Lys Pro Arg Glu
            260                 265                 270
Glu Gln Tyr Asn Ser Thr Tyr Arg Val Val Ser Val Leu Thr Val Leu
        275                 280                 285
His Gln Asp Trp Leu Asn Gly Lys Glu Tyr Lys Cys Lys Val Ser Asn
    290                 295                 300
Lys Ala Leu Pro Ala Pro Ile Glu Lys Thr Ile Ser Lys Ala Lys Gly
305                 310                 315                 320
Gln Pro Arg Glu Pro Gln Val Tyr Thr Leu Pro Pro Ser Arg Asp Glu
                325                 330                 335
Leu Thr Lys Asn Gln Val Ser Leu Thr Cys Leu Val Lys Gly Phe Tyr
            340                 345                 350
Pro Ser Asp Ile Ala Val Glu Trp Glu Ser Asn Gly Gln Pro Glu Asn
        355                 360                 365
Asn Tyr Lys Thr Thr Pro Pro Val Leu Asp Ser Asp Gly Pro Phe Phe
    370                 375                 380
Leu Tyr Ser Lys Leu Thr Val Asp Lys Ser Arg Trp Gln Gln Gly Asn
385                 390                 395                 400
Val Phe Ser Cys Ser Val Met His Glu Ala Leu His Asn His Tyr Thr
                405                 410                 415
Gln Lys Ser Leu Ser Leu Ser Pro Gly Lys
            420                 425

<210> SEQ ID NO 5
<211> LENGTH: 1134
<212> TYPE: DNA
<213> ORGANISM: Artificial
<220> FEATURE:
<223> OTHER INFORMATION: DNA encoding rHuGMCSF-FcG fusion protein
```

<400> SEQUENCE: 5

```
atgtggctgc agagcctgct gctcttgggc actgtggcct gcagcatctc tgcacccgcc    60
cgctcgccca gccccagcac gcagccctgg gagcatgtga atgccatcca ggaggcccgg   120
cgtctcctga acctgagtag agacactgct gctgagatga atgaaacagt agaagtcatc   180
tcagaaatgt ttgacctcca ggagccgacc tgcctacaga cccgcctgga gctgtacaag   240
cagggcctgc ggggcagcct caccaagctc aagggcccct tgaccatgat ggccagccac   300
tacaagcagc actgccctcc aaccccggaa acttcctgtg caacccagat tatcaccttt   360
gaaagtttca agagaaacct gaaggacttt ctgcttgtca tccccttga ctgctgggag    420
ccagtccagg aggttgagcc caaatctggt gacaaaacta gtacatgccc accgtgccca   480
gcacctgaac tcctgggggg accgtcagtc ttcctcttcc ccccaaaacc caaggacacc   540
ctcatgatct cccggacccc tgaggtcaca tgcgtggtgg tggacgtgag ccacgaagac   600
cctgaggtca agttcaactg gtacgtggac ggcgtggagg tgcataatgc caagacaaag   660
ccgcgggagg agcagtacaa cagcacgtac cgtgtggtca gcgtcctcac cgtcctgcac   720
caggactggc tgaatggcaa ggagtacaag tgcaaggtct ccaacaaagc cctcccagcc   780
cccatcgaga aaaccatctc caaagccaaa gggcagcccc gagaaccaca ggtgtacacc   840
ctgcccccat cccgggatga gctgaccaag aaccaggtca gcctgacctg cctggtcaaa   900
ggcttctatc ccagcgacat cgccgtggag tgggagagca atgggcagcc ggagaacaac   960
tacaagacca cgcctcccgt gctggactcc gacggcccct tcttcctcta cagcaagctc  1020
accgtggaca gagcaggtg gcagcagggg aacgtcttct catgctccgt gatgcatgag  1080
gctctgcaca accactacac gcagaagagc ctctccctgt ctccgggtaa ataa        1134
```

<210> SEQ ID NO 6
<211> LENGTH: 377
<212> TYPE: PRT
<213> ORGANISM: Artificial
<220> FEATURE:
<223> OTHER INFORMATION: amino acid sequence of rHuGMCSF-FcG fusion protein

<400> SEQUENCE: 6

```
Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

Val Glu Pro Lys Ser Gly Asp Lys Thr Ser Thr Cys Pro Pro Cys Pro
```

```
        145                 150                 155                 160
Ala Pro Glu Leu Leu Gly Gly Pro Ser Val Phe Leu Phe Pro Pro Lys
                    165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Lys Phe Asn Trp Tyr
            195                 200                 205

Val Asp Gly Val Glu Val His Asn Ala Lys Thr Lys Pro Arg Glu Glu
        210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Asp Glu Leu
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Pro Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
        355                 360                 365

Lys Ser Leu Ser Leu Ser Pro Gly Lys
    370                 375
```

<210> SEQ ID NO 7
<211> LENGTH: 40
<212> TYPE: DNA
<213> ORGANISM: Artificial
<220> FEATURE:
<223> OTHER INFORMATION: oligonucleotide primer

<400> SEQUENCE: 7
ccggaattcg ccaccatggg ggtgcacgaa tgtcctgcct                              40

<210> SEQ ID NO 8
<211> LENGTH: 42
<212> TYPE: DNA
<213> ORGANISM: Artificial
<220> FEATURE:
<223> OTHER INFORMATION: oligonucleotide primer

<400> SEQUENCE: 8
ttttcctttt gcggccgctt atttacccgg agacagggag ag                          42

<210> SEQ ID NO 9
<211> LENGTH: 45
<212> TYPE: DNA
<213> ORGANISM: Artificial
<220> FEATURE:
<223> OTHER INFORMATION: oligonucleotide primer

<400> SEQUENCE: 9
aggcctgcag gacaggggac agagttgagc ccaaatctgg tgaca                       45

<210> SEQ ID NO 10
<211> LENGTH: 45
<212> TYPE: DNA
<213> ORGANISM: Artificial
<220> FEATURE:
<223> OTHER INFORMATION: oligonucleotide primer

<400> SEQUENCE: 10
tgtcaccaga tttgggctca actctgtccc ctgtcctgca ggcct                45

<210> SEQ ID NO 11
<211> LENGTH: 45
<212> TYPE: DNA
<213> ORGANISM: Artificial
<220> FEATURE:
<223> OTHER INFORMATION: oligonucleotide primer

<400> SEQUENCE: 11
aggcctgcag gacaggggac agagttgagc ccaaatcttg tgaca                45

<210> SEQ ID NO 12
<211> LENGTH: 45
<212> TYPE: DNA
<213> ORGANISM: Artificial
<220> FEATURE:
<223> OTHER INFORMATION: oligonucleotide primer

<400> SEQUENCE: 12
tgtcacaaga tttgggctca actctgtccc ctgtcctgca ggcct                45

<210> SEQ ID NO 13
<211> LENGTH: 56
<212> TYPE: DNA
<213> ORGANISM: Artificial
<220> FEATURE:
<223> OTHER INFORMATION: oligonucleotide primer

<400> SEQUENCE: 13
actgaattcg ccaccatgtg gctgcagagc ctgctgctct tgggcactgt ggcctg     56

<210> SEQ ID NO 14
<211> LENGTH: 42
<212> TYPE: DNA
<213> ORGANISM: Artificial
<220> FEATURE:
<223> OTHER INFORMATION: oligonucleotide primer

<400> SEQUENCE: 14
ttttcctttt gcggccgctt atttacccgg agacagggag ag                   42

<210> SEQ ID NO 15
<211> LENGTH: 50
<212> TYPE: DNA
<213> ORGANISM: Artificial
<220> FEATURE:
<223> OTHER INFORMATION: oligonucleotide primer

<400> SEQUENCE: 15
gactgctggg agccagtcca ggaggttgag cccaaatctg gtgacaaaac            50

<210> SEQ ID NO 16
<211> LENGTH: 50
<212> TYPE: DNA
<213> ORGANISM: Artificial
<220> FEATURE:

<223> OTHER INFORMATION: oligonucleotide primer

<400> SEQUENCE: 16
gttttgtcac cagatttggg ctcaacctcc tggactggct cccagcagtc          50

<210> SEQ ID NO 17
<211> LENGTH: 14
<212> TYPE: PRT
<213> ORGANISM: Artificial Sequence
<220> FEATURE:
<223> OTHER INFORMATION: Synthetic linker oligopeptide

<400> SEQUENCE: 17

Gly Gly Ser Gly Gly Ser Gly Gly Gly Ser Gly Gly Gly Ser
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Synthetic peptide linker

<400> SEQUENCE: 18

Gly Ser Gly Gly Gly Ser Gly Gly Gly Ser Gly Gly Gly Ser Gly Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide linker

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide linker

<400> SEQUENCE: 20

Gly Gly Gly Gly Ser Gly Gly Gly Gly Gly Ser
1               5                   10

<210> SEQ ID NO 21
<211> LENGTH: 10
<212> TYPE: DNA
<213> ORGANISM: Artificial Sequence
<220> FEATURE:
<223> OTHER INFORMATION: the Kozak sequence

<400> SEQUENCE: 21
gccaccatgg          10

<210> SEQ ID NO 22
<211> LENGTH: 15
<212> TYPE: PRT
<213> ORGANISM: Artificial Sequence
<220> FEATURE:
<223> OTHER INFORMATION: 15 terminal amino acids of pure rHuEPO-FcG
      sequence

```
<400> SEQUENCE: 22

Ala Pro Pro Arg Leu Ile Cys Asp Ser Arg Val Leu Glu Arg Tyr
1               5                   10                  15

<210> SEQ ID NO 23
<211> LENGTH: 10
<212> TYPE: PRT
<213> ORGANISM: Artificial Sequence
<220> FEATURE:
<223> OTHER INFORMATION: mutated IgG1 hinge sequence C-terminal from
      cysteine point mutation

<400> SEQUENCE: 23

Asp Lys Thr Ser Thr Cys Pro Pro Cys Pro
1               5                   10

<210> SEQ ID NO 24
<211> LENGTH: 16
<212> TYPE: PRT
<213> ORGANISM: Artificial Sequence
<220> FEATURE:
<223> OTHER INFORMATION: mutated IgG1 hinge sequence

<400> SEQUENCE: 24

Val Glu Pro Lys Ser Gly Asp Lys Thr Ser Thr Cys Pro Pro Cys Pro
1               5                   10                  15
```